US010047133B2

(12) United States Patent
Kungl

(10) Patent No.: US 10,047,133 B2
(45) Date of Patent: Aug. 14, 2018

(54) GLYCOSAMINOGLYCAN-ANTAGONISING FUSION PROTEINS AND METHODS OF USING SAME

(71) Applicant: ANTAGONIS BIOTHERAPEUTICS GMBH, Graz (AT)

(72) Inventor: Andreas Kungl, Graz (AT)

(73) Assignee: Antagonis Biotherapeutics GmbH, Graz (AT)

( * ) Notice: Subject to any disclaimer, the term of this patent is extended or adjusted under 35 U.S.C. 154(b) by 0 days.

(21) Appl. No.: 15/113,394

(22) PCT Filed: Jan. 22, 2015

(86) PCT No.: PCT/EP2015/051246
§ 371 (c)(1),
(2) Date: Jul. 21, 2016

(87) PCT Pub. No.: WO2015/110526
PCT Pub. Date: Jul. 30, 2015

(65) Prior Publication Data

US 2017/0058012 A1 Mar. 2, 2017

(30) Foreign Application Priority Data

Jan. 22, 2014 (EP) .................................... 14152167
Dec. 23, 2014 (EP) .................................... 14200116

(51) Int. Cl.
*C07K 14/52* (2006.01)
*A61K 38/19* (2006.01)
*C07K 14/54* (2006.01)
*A61K 38/00* (2006.01)

(52) U.S. Cl.
CPC ........ *C07K 14/5421* (2013.01); *C07K 14/521* (2013.01); *C07K 14/523* (2013.01); *A61K 38/00* (2013.01); *C07K 2319/31* (2013.01)

(58) Field of Classification Search
CPC ... C07K 14/5421; C07K 14/523; A61K 38/00
See application file for complete search history.

(56) References Cited

U.S. PATENT DOCUMENTS 5,116,964 A * 5/1992 Capon .................. C07K 14/705 424/134.1
2003/0162737 A1 8/2003 Egashira et al.
2007/0036750 A1 2/2007 Chou et al.
2011/0280873 A1 11/2011 Presta et al.

FOREIGN PATENT DOCUMENTS

WO 2005/054285 A1 6/2005
WO 2009/015884 A1 2/2009
WO 2009/126920 A2 10/2009
WO 2010/086426 A1 8/2010
WO 2011/079004 A1 6/2011
WO 2011/124718 A1 10/2011

OTHER PUBLICATIONS

Alcami et al, "Blockade of Chemokine Activity by a Soluble Chemokine Binding Protein from Vaccinia Virus", J. Immunol. 160 (2), 624-33, 1998.
Ali et al, "Multimerization of monocyte chemoattractant protein-1 is not required for glycosaminoglycan-dependent transendothelial chemotaxis", Biochem.J. 358, 737-745, 2001.
Aukrust et al, "Elevated Circulating Levels of C-C Chemokines in Patients with Congestive Heart Failure", Circulation 97, 1136-1143, 1998.
Baggiolini M., "Chemokines in pathology and medicine", J. Int. Med. 250, 91-104, 2001.
Boring et al, Molecular Cloning and Functional Expression of Murine JE (Monocyte Chemoattractant Protein 1) and Murine Macrophage Inflammatory Protein 1a Receptors; Evidence for Two Closely Linked C-C Chemokine Receptors on Chromosome 9:, J. Biol. Chem. 271 (13), 7551-7558, 1996.
Falsone et al, "Designing CXCL8-based decoy proteins with strong anti-inflammatory activity in vivo", Bioscience Reports, 2013, No. 33, pp. 743-754.
Fernandez et al, "Structure, Function, and Inhibition of Chemokines", 2002, Annual review of pharmacology and toxicology, 42, 469-499.
Flory et al, "Pulmonary Granuloma Formation in the Rat is Partially Dependent on Monocyte Chemoattractant Protein 1", 1. Lab. Invest. 69 (4), 396-404, 1993.
Gerlza et al, "A Combinatorial Approach to Biophysically Characterise Chemokine-Glycan Binding Affinities for Drug Development", (2014). Molecules 19, 10618-10634.
Goger et al, "Different Affinities of Glycosaminoglycan Oligosaccharides for Monomeric and Dimeric Interleukin-8: A Model for Chemokine Regulation at Inflammatory Sites", 2002, Biochemistry, 41, 1640-1646.
Gong et al, "An Antagonis of Monocyte Chemoattractant Protein 1 (MCP-1) Inhibits Arthritis in the MRL-Ipr Mouse Model", J.Exp. Med. 186 (1), 131-7, 1997.
Gosling et al, "MCP-1 deficiency reduces susceptibility to atherosclerosis in mice that overexpress human apolipoprotein B", J. Clin. Invest. 103 (6), 773-8, 1999.
Grewal et al, "Transgenic Monocyte Chemoattractant Protein-1 (MCP-1) in Pancreativ Islets Produces Monocyte-Rich Insulitis Without Diabetes", J. Immunol. 159 (1), 401-408, 1997.
Gupta et al, "A potent inhibitor of endothelial cell proliferation is generated by proteolytic cleavage of the chemokine platelet factor 4" Proc.Natl.Acad.Sci., USA, 92, (17), 7799-7803, 1995.

(Continued)

*Primary Examiner* — Prema Mertz
(74) *Attorney, Agent, or Firm* — Loza & Loza, LLP; Michael Fedrick

(57) ABSTRACT

The present invention relates to novel monomeric fusion proteins derived from human GAG binding proteins such as chemokines with increased glycosaminoglycan (GAG) binding affinity and knocked-out or reduced GPCR activity compared to wild type GAG binding proteins, which are highly selectively competitive and are of increased bioavailability, and to their use for prevention or treatment of pathological cell movement as in metastasis.

10 Claims, 17 Drawing Sheets

(56) References Cited

OTHER PUBLICATIONS

Figure 2:
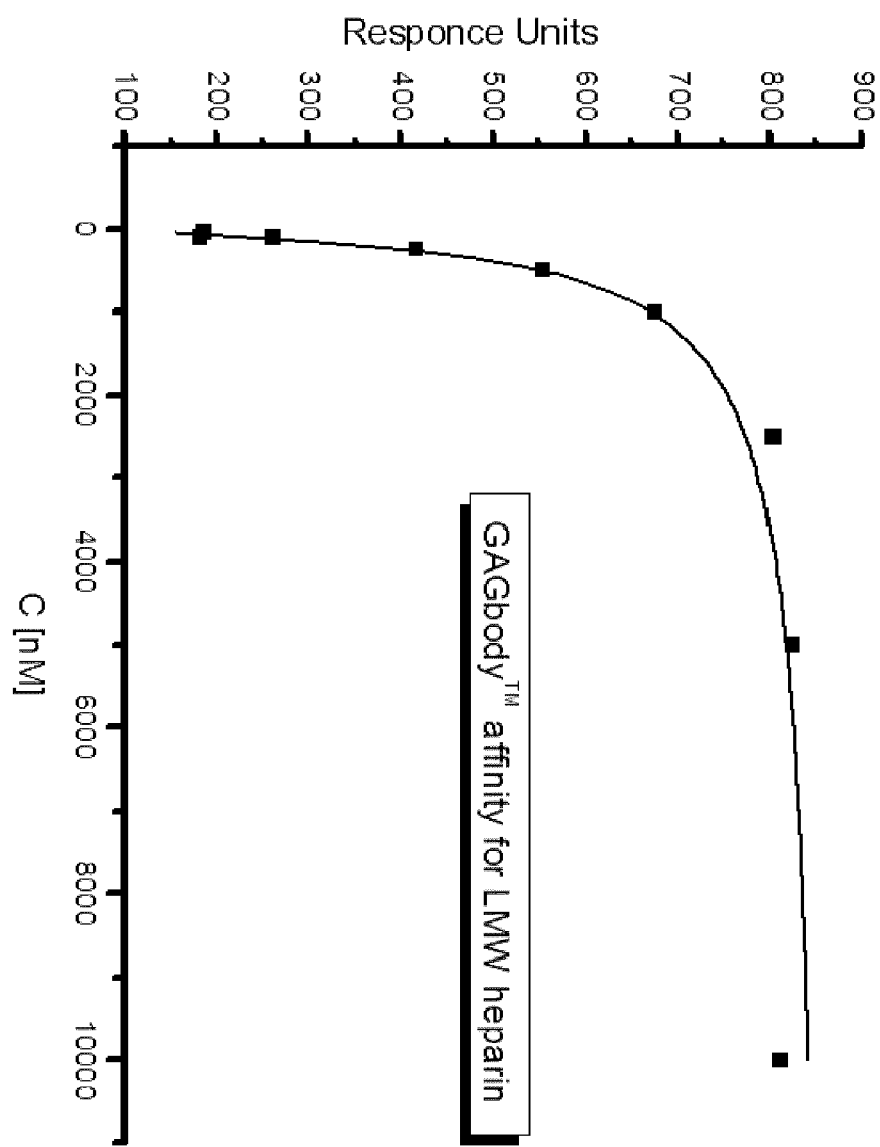

Hemmerich et al, "Identification of Residues in the Monocyte Chemotactic Protein-1 That Contact the MCP-1 Receptor, CCR2", Biochemistry 38 (40), 13013-13025, 1999.
Hohensinner et al, "Monocyte chemoattractant protein (MCP-1) is expressed in human cardiac cells and is differentially regulated by inflammatory mediators and hypoxia", FEBS Letters 580, 3532-3538, 2006.
Hosaka et al, "Expression of the chemokine superfamily in rheumatoid arthritis", Clin. Exp. Immunol. 97(3), 451-457, 1994.
Jansma et al, "Homo- and Hetero-Oligomerization of Chemokines", 2009, Methods in Enzymology. Academic Press, pp. 31-50.
Janargin et al, "Identification of Surface Residues of the Monocyte Chemotactic Protein 1 That Affect Signaling through the Receptor CCR2", Biochemistry, 38, 16167-16177, 1999.
Koch et al, "Enhanced Production of Monocyte Chemoattractant Protein-1 in Rheumatoid Arthritis", J. Clin. Invest. 90, 772-779, 1992.
Kuziel et al, "Severe reduction in leukocyte adhesion and monocyte extravasation in mice deficient in CC chemokine receptor 2", Proc.Natl.Acad.Sci. USA 94 (22), 12053-8, 1997.
Lau et al, "Identification of the Glycosaminoglycan Binding Site of the CC Chemokine, MCP-1", J. Biol. Chem., 279(21), 22294-22305, 2004.
Liehn et al, "A New Monocyte Chemotactic Protein-1/ Chemokine CC Motif Ligand-2 Competitor Limiting Neointima Formation and Myocardial Ischemia/Reperfusion Injury in Mice", J. Am. Coll. Cardiol., 23:56(22)1847-57, 2010.
Lu et al, Abnormalities in Monocyte Recruitment and Cytokine Expression in Monocyte Chemoattractant Protein 1-deficient Mice:, J. Exp.Med. 187 (4), 601-8, 1998.
Lubkowski et al, "The structure of MCP-1 in two crystal forms provides a rare example of variable quaternary interactions", Nature Structural Biology, 4, 1, 1997, 64-69.
Lukacs et al, "Differential Recruitment of Leukocyte Populations and Alteration of Airway Hyperreactivity by C-C Family Chemokines in Allergic Airway Inflammation", J.Immunol., 158 (9), 4398-4404, 1997.
MacDermott, Richard P "Chemokines in the Inflammatory Bowel Diseases" J. Clin. Immunol. 19, 266-272, 1999.
Nelken et al, "Monocyte Chemoattractant Protein-1 in Human Atheromatous Plaques", J. Clin. Invest. 88, 1121-1127, 1991.
Paavola et al, "Monomeric Monocyte Chemoattractant Protein-1 (MCP-1) Binds and Activates the MCP-1 Receptor CCR2B", J. Biol. Chem., 273 (50), 33157-33165, 1998.
Piccinini et al, "Rationally Evolving MCP-1/CCL2 into a Decoy Protein with Potent Anti-inflammatory Activity in Vivo", (2010) J Biol Chem 285, 8782-8792.
Proudfoot et al, "Glycosaminoglycan binding and oligomerization are essential for the in vivo activity of certain chemokines" Proc. Natl.Acad.Sci., 100, 4, 2003, 1885-1890.
Qian et al, "CCL2 recruits inflammatory monocytes to facilitate breast tumor metastasis", (2011) Nature 475, 222-225.
Robinson et al, "Chemokine expression in rheumatoid arthritis (RA): evidence of RANTES and macrophage inflammatory protein (MIP)-1,3 production by synovial T cells" Clin. Exp. Immunol. 101(3), 398-407, 1995.
Steitz et al, "Mapping of MCP-1 functional domains by peptide analysis and site-directed mutagenesis", FEBS Letters, 430, 3, 1998, 158-164.
Wolf et al, "Endothelial CCR2 Signaling Induced by Colon Carcinoma Cells Enables Extravasation via the JAK2-Stat5 and p38MAPK Pathway" (2012) Cancer Cell 22, 91-105.
Yla-Herttuala et al, "Expression of monocyte chemoattractant protein 1 in macrophage-rich areas of human and rabbit atherosclerotic lesions", Proc. Natl. Acad. Sci USA 88, 5252-5256, 1991.
Zisman et al, "MCP-1 Protects Mice in Lethal Endotoxemia", J.Clin.Invest. 99 (12), 2832-6, 1997.
International Search Report for PCT/EP15/51246 dated Apr. 16, 2015; 10 pages.
Written Opinion for PCT/EP15/51246 dated Apr. 16, 2015; 9 pages.
International Preliminary Report on Patentability for PCT/EP15/51246 dated Jul. 26, 2016; 9 pages.

* cited by examiner

Fig 1A wtMCP1

QPDAINAPVTCCYNFTNRKISVQRLASYRRITSSKCPKEAVIFKTIVAKEICADPK
QKWVQDSMDHLDKQTQTPKT (SEQ ID. No. 1)

ATG01:

DAHKSEVAHRFKDLGEENFKALVLIAFAQYLQQAPFEDHVKLVNEVTEFAKTC
VADESAENCDKSLHTLFGDKLCTVATLRETYGEMADCCAKQEPERNECFLQHKDDN
PNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRF
PKAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARRH
PDYSVVLLLRLAKTYETTLEKCCAAADPHECYAKVFDEFKPLVEEPQNLIKQNCELFE
QLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFH
ADICTLSEKERQIKKQTALVELVKHKPKATKEQLKAVMDDFAAFVEKCCKADDKETCF
AEEGKKLVAASQAALGL*GGGGS*MQPDAINAPVTCCAQFTKRKIKVKRLASYRRITS**K
KCPKEAVIFKTIVAKEICADPKQKWVQDSMDHLDKQTQTPKT

(SEQ ID No. 2)

ATG02:

DAHKSEVAHRFKDLGEENFKALVLIAFAQYLQQAPFEDHVKLVNEVTEFAKTC
VADESAENCDKSLHTLFGDKLCTVATLRETYGEMADCCAKQEPERNECFLQHKDDN
PNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRF
PKAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARRH
PDYSVVLLLRLAKTYETTLEKCCAAADPHECYAKVFDEFKPLVEEPQNLIKQNCELFE

Fig 1B

QLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFH
ADICTLSEKERQIKKQTALVELVKHKPKATKEQLKAVMDDFAAFVEKCCKADDKETCF
AEEGKKLVAASQAALGL*GGGGS*MQPDAINAPVTCCAQFTNRKIKVKRLASYRRITSS
KCPKEAVIFKTIVAKEICADPKQKWVQDSMDHLDKQTQTPKT (SEQ ID No. 3)

HSA:

DAHKSEVAHRFKDLGEENFKALVLIAFAQYLQQAPFEDHVKLVNEVTEFAKTC
VADESAENCDKSLHTLFGDKLCTVATLRETYGEMADCCAKQEPERNECFLQHKDDN
PNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRF
PKAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARRH
PDYSVVLLLRLAKTYETTLEKCCAAADPHECYAKVFDEFKPLVEEPQNLIKQNCELFE
QLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFH
ADICTLSEKERQIKKQTALVELVKHKPKATKEQLKAVMDDFAAFVEKCCKADDKETCF
AEEGKKLVAASQAALGL (SEQ ID No. 4)

wt-HSA:

DAHKSEVAHRFKDLGEENFKALVLIAFAQYLQQCPFEDHVKLVNEVTEFAKTC
VADESAENCDKSLHTLFGDKLCTVATLRETYGEMADCCAKQEPERNECFLQHKDDN
PNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRF
PKAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARRH
PDYSVVLLLRLAKTYETTLEKCCAAADPHECYAKVFDEFKPLVEEPQNLIKQNCELFE
QLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFH

Fig 1C

ADICTLSEKERQIKKQTALVELVKHKPKATKEQLKAVMDDFAAFVEKCCKADDKETCF
AEEGKKLVAASQAALGL (SEQ ID No. 6)

wtIL8:

SAKELRCQCIKTYSKPFHPKFIKELRVIESGPHCANTEIIVKLSDGRELCLDPKE
NWVQRVVEKFLKRAENS (SEQ ID No. 7)

ATG03

DAHKSEVAHRFKDLGEENFKALVLIAFAQYLQQAPFEDHVKLVNEVTEFAKTC
VADESAENCDKSLHTLFGDKLCTVATLRETYGEMADCCAKQEPERNECFLQHKDDN
PNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRF
PKAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARRH
PDYSVVLLLRLAKTYETTLEKCCAAADPHECYAKVFDEFKPLVEEPQNLIKQNCELFE
QLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFH
ADICTLSEKERQIKKQTALVELVKHKPKATKEQLKAVMDDFAAFVEKCCKADDKETCF
AEEGKKLVAASQAALGLGGGGSCQCIKTYSKPFHPKFIKELRVIESGPHCANTEIIVKL
SDGRELCLDPKENWVQRVVEKFLKRAKKS (SEQ ID No. 8)

GLYCOSAMINOGLYCAN-ANTAGONISING FUSION PROTEINS AND METHODS OF USING SAME

CROSS-REFERENCE TO RELATED APPLICATIONS

This application is the U.S. national stage of International Patent Application No. PCT/EP2015/051246, filed on Jan. 22, 2015 and entitled NOVEL GLYCOSAMINOGLYCAN-ANTAGONISING FUSION PROTEINS AND METHODS OF USING SAME, which claims the benefit of priority under 35 U.S.C. § 119 from European Patent Application No. 14200116.3, filed on Dec. 23, 2014, and from European Patent Application No. 14152167.4, filed on Jan. 22, 2014. The disclosures of the foregoing applications are incorporated herein by reference in their entirety.

SEQUENCE LISTING

The entire content of a Sequence Listing titled "Sequence_ Listing.txt," created on Feb. 21, 2017 and having a size of 40 kilobytes, which has been submitted in electronic form in connection with the present application, is hereby incorporated by reference herein in its entirety.

BACKGROUND

The present invention relates to novel monomeric fusion proteins derived from human GAG binding proteins such as chemokines with increased glycosaminoglycan (GAG) binding affinity and knocked-out or reduced G-protein coupled receptor (GPCR) activity compared to wild type GAG binding proteins fused to human serum albumin, which are highly selectively competitive and are of increased bioavailability, and to their use for prevention or treatment of pathological cell movement as in metastasis.

Chemokines are well-known key players in the immune system and in the process of angiogenesis and are also involved in pathological conditions like cancer. The interaction with cell-surface heparan sulfate proteoglycans is essential for their signaling via G-protein coupled receptors.

Chemokines stand for a large group of small cytokines. Their name is the result of their ability to induce chemotaxis or the directed movement of cells through a concentration gradient: chemotactic cytokines. The first chemokine to be characterized was Interleukin 8 in 1987. Nowadays there are about 50 known ligands, 18 standard receptors and 5 atypical receptors of the human chemokine family. In their monomeric form their molecular weight of the ligands ranges from 8-12 kDa, the receptors are about 40 kDa. It was found that chemokine genes tend to form specific clusters on certain chromosomal sites.

All chemokines, with the exception of lymphotactin and fraktaline/neurotactin which are members of the C and CX3C chemokine subfamily, respectively, have four cysteines in conserved positions and can be divided into the CXC or α-chemokine and the CC or β-chemokine subfamilies on the basis of the presence or absence, respectively, of an amino acid between the two cysteines within the N-terminus. Chemokines are small secreted proteins that function as intercellular messengers to orchestrate activation and migration of specific types of leukocytes from the lumen of blood vessels into tissues (Baggiolini M., J. Int. Med. 250, 91-104 (2001)). This event is mediated by the interaction of chemokines with seven transmembrane G-protein-coupled receptors (GPCRs) on the surface of target cells. Such interaction occurs in vivo under flow conditions. Therefore, the establishment of a local concentration gradient is required and ensured by the interaction of chemokines with cell surface glycosaminoglycans (GAGs). Chemokines have two major sites of interaction with their receptors, one in the N-terminal domain which functions as a triggering domain, and the other within the exposed loop after the second cysteine, which functions as a docking domain (Gupta S. K. et al., Proc. Natl. Acad. Sci., USA, 92, (17), 7799-7803 (1995)). The GAG binding sites of chemokines comprise clusters of basic amino acids spatially distinct (Ali S. et al., Biochem. J. 358, 737-745 (2001)). Some chemokines, such as RANTES, have the BBXB motif in the 40 s loop as major GAG binding site; IL-8 interacts with GAGs through the C-terminal α-helix and Lys 20 in the proximal N-loop. Other chemokines, such as MCP-1, show a significant overlap between the residues that comprise the receptor binding and the GAG binding site (Lau E. K. et al., J. Biol. Chem., 279 (21), 22294-22305 (2004)).

IL (interleukin)-8 (CXCL8, CXC chemokine ligand 8)) is an 8 kDa CXC-chemokine that attracts neutrophils to sites of inflammation when immobilized on endothelial GAG chains in the vasculature. The subsequent binding of the chemokine to the neutrophil GPCRs (G-protein coupled receptors), CXCR1 (CXC chemokine receptor 1) and CXCR2, fully activates the already slowed down (selectin-mediated 'rolling') neutrophil and leads to firm adhesion and subsequent transmigration through the blood vessel endothelium into the tissue. The three-dimensional solution structure of CXCL8 shows a dimer with two symmetry-related, antiparallel α-helices, which lie on top of six-stranded antiparallel β-sheets derived from two three-stranded Greek keys, one from each monomer unit. Despite its small size, CXCL8 exhibits discrete but connected structural domains by which the chemokine interacts with its two biological receptors: with the traditional GPCRs CXCR1 and CXCR2 on the one hand and with GAG co-receptors on the other hand (Falsone A. et al., Biosci. Rep., 2013, 33(5), e00068).

In the context of the chemokine-β family of cytokines, monocyte chemoattractant protein-1 (MCP-1) is a monocyte and lymphocyte-specific chemoattractant and activator found in a variety of diseases that feature a monocyte-rich inflammatory component, such as atherosclerosis (Nelken N. A. et al., J. Clin. Invest. 88, 1121-1127 (1991); Yla-Herttuala, S., Proc. Natl. Acad. Sci USA 88, 5252-5256 (1991), rheumatoid arthritis (Koch A. E. et al., J. Clin. Invest. 90, 772-779 (1992); Hosaka S. et al., Clin. Exp. Immunol. 97(3), 451-457 (1994), Robinson E. et al., Clin. Exp. Immunol. 101(3), 398-407 (1995)), inflammatory bowel disease (MacDermott R. P. et al., J. Clin. Immunol. 19, 266-272 (1999)) and congestive heart failure (Aukrust P., et al., Circulation 97, 1136-1143 (1998), Hohensinner P. J. et al., FEBS Letters 580, 3532-3538 (2006)). Crucially, knockout mice that lack MCP-1 or its receptor CCR2, are unable to recruit monocytes and T-cells to inflammatory lesions (Grewal I. S. et al., J. Immunol. 159 (1), 401-408 (1997); Boring L. et al., J. Biol. Chem. 271 (13), 7551-7558 (1996); Kuziel W. A., et al., Proc. Natl. Acad. Sci. USA 94 (22), 12053-8 (1997); Lu B., et al., J. Exp. Med. 187 (4), 601-8 (1998)); furthermore, treatment with MCP-1 neutralizing antibodies or other biological antagonists can reduce inflammation in several animal models (Lukacs N. W. et al., J. Immunol., 158 (9), 4398-4404 (1997); Flory C. M. et al., 1. Lab. Invest. 69 (4), 396-404 (1993); Gong J. H., et al., J. Exp. Med. 186 (1), 131-7 (1997); Zisman D. A. et al., J. Clin. Invest. 99 (12), 2832-6 (1997)). Finally, LDL-receptor/MCP-1-deficient and apoB-transgenic/MCP-1-deficient mice show considerably less lipid deposition and macrophage accumulation throughout their aortas compared to the WT MCP-1 strains (Alcami A. et al., J. Immunol. 160 (2), 624-33 (1998); Gosling J. et al., J. Clin. Invest. 103 (6), 773-8 (1999)).

Piccinini et al. have shown the effect of a limited number of site-directed MCP-1 mutants on enhanced glycosaminoglycan binding (J Biol Chem. 2010 Jan. 22). Liehn et al. have shown that increasing the GAG binding affinity has a therapeutic effect in murine models of myocardiac infarction and restenosis (J. Am. Coll. Cardiol., 23:56(22):1847-57, 2010).

Proudfoot et al. (Proc. Natl. Acad. Sci., 100, 4, 2003, 1885-1890) investigated the effect of mutations in the GAG binding sites of chemokines, amongst others of MCP-1. The specific mutant (18AA19)-MCP-1 shows only residual affinity for heparin.

US2003/0162737 discloses an antagonistic MCP-1 mutein for the treatment of pulmonary hypertension. Said MCP-1 mutein comprises several deletions at the N-terminus of the protein, up to deletion of N-terminal amino acids 1-10 or 2-8. Further the mutein can comprise a modification at amino acid positions 22 or 24.

Steitz S. et al. (FEBS Letters, 430, 3, 1998, 158-164) investigated the role of N-terminal modifications on receptor binding. MCP-1 mutants comprising substitutions of amino acid positions 13 and 18 were disclosed. Y13A showed a dramatic loss in function to induce THP-1 chemotaxis.

Lubkowski J. et al. (Nature Structural Biology, 4, 1, 1997, 64.69) investigated the x-ray crystal structure of recombinant human MCP-1. The N-terminus of the protein was modified and its effect on activity was measured. It was shown that modification specifically at positions 10 and 13 lowered the activity of MCP-1 and had an effect on the dimer stabilization. An impaired chemotactic activity of the mutants suggested a functional significance for Tyr28, Arg 29, Arg30 and Asp68. It was noted that charged amino acids (Arg, Asp) destabilize an alternate dimer and that the introduction of uncharged residues can significantly increase stability.

WO2010086426A1 describes modified MCP-1 mutant proteins with increased GAG binding affinity.

US20110280873A1 reports the development of MCP-1 Ig fusion polypeptides for treating diseases.

US20070036750A1 also discloses MCP-1 fusion proteins linked to immunoglobulins and their use to treat medical disorders.

WO2008074047 describes chemokine proteins fused to a chaperone peptide, e.g. heat shock proteins.

WO2005054285A1 describes chemokine mutants. One example is modified IL-8 containing amino acid substitutions at selected positions.

Since the first chemokines and their receptors have been identified, the interest on exactly understanding their roles in normal and diseased physiology has become more and more intense. The constant need for new drugs with modes of action different from those of existing drugs support the development of new protein-based GAG-antagonists and their use in therapeutic applications, specifically for the prevention and treatment of cancer metastasis.

Although several proteins with increased GAG binding affinity and reduced receptor binding activity had been developed in the past, there is still need to develop proteins which show selective competition in GAG binding and thus can avoid negative side effects due to unselective binding affinity. Since for most of the GAG-binding proteins the exact binding epitope on the glycan is not known, targeting of such specific epitopes is still very challenging. It has been found in the past that engineering additional basic amino acids at many positions into a given GAG-binding protein can lead to the unwanted displacement of many proteins from a typical GAG co-receptor molecule on top of the target GAG-binding protein. In addition, oligomerisation of a GAG-binding protein can cause further unwanted and unspecific displacement reactions. Furthermore, therapeutic GAG-binding proteins should exhibit a serum half life which avoids daily dosing.

SHORT DESCRIPTION OF THE INVENTION

The problem is solved by the embodiment of the present invention.

Recombinant GAG binding fusion protein variants that compete with their wild type counterpart for glycosaminoglycan binding and show reduced or knocked out activation of leukocytes have been generated, which are highly advantageous due to their
  a) Increased serum half life and bioavailability due to HSA fusion tag
  b) Lack of oligomerisation, thus these mutants are monomeric proteins which show inhibited or lack of aggregation of monomers
  c) Comprise highly selective competition Additionally, said proteins may also show decreased glycosylation pattern which for example may result from protein expression in cell culture systems like *Pichia pastoris*.

MCP-1 and IL-8 (interleukin 8) mutants with a higher GAG binding affinity either by modifying the wild type GAG binding region or by introducing a new GAG binding region into the MCP1 protein and simultaneously knocking out or reducing its GPCR activity, specifically the CCR2 activity of the chemokine have been described in WO2009015884A1.

WO2009015884A1 and WO2010086426A1 describe MCP-1 proteins wherein a region of the MCP-1 protein is modified in a structure conserving way by introducing basic and/or electron donating amino acids or replacing native amino acids with basic and/or electron donating amino acids and optionally also modifying the N-terminal region of said MCP-1 protein by addition, deletion and/or replacement of amino acids and, optionally, adding an N-terminal Methionine (M) to the mutant MCP-1 protein, resulting in partial or complete loss of chemotactic activity have been disclosed there. This first generation GAG-binding CCL2 decoy protein contained two amino acid replacements (S21K and Q23R), which were introduced to increase GAG-binding affinity, as well as Y13A and an N terminal methionine addition to block CCR2 activation. For the second generation of CCL2-based therapeutic mutant proteins, further basic amino acids were introduced into the chemokine sequence in order to further enhance the GAG binding affinity. It consists of 77 amino acids and therefore a short serum half-life was expected.

WO2005054285 describes IL-8 mutants wherein a region of the IL-8 protein is modified in a structure conserving way by introducing basic and/or electron donating amino acids or replacing native amino acids with basic and/or electron donating amino acids and optionally also modifying the N-terminal region of said IL-8 protein by addition, deletion and/or replacement of amino acids, resulting in partial or complete loss of chemotactic activity have been disclosed there. Specifically, IL-8 mutants are disclosed wherein positions 17, 21, 70 and/or 71 are substituted by foreign amino acids. Due to its length of 73 amino acids a short serum half-life was expected.

Specifically for chronic indications, however, the inventors aimed to extend the proteins' serum half-life as they expect it to be parenterally applied.

Specifically, this was achieved by C-terminal fusion of a CCL2-based decoy protein to human serum albumin which improved not only in vivo parameters but surprisingly also the chemokine displacement pattern and its oligomerization behavior compared to the unfused decoy protein.

Novel fusion decoy proteins with high therapeutic value developed by the inventive method are called GAGbody (ATG01) and ATG02 as they aim to target specific GAG structures in a similar way as antibodies target antigens.

The inventors also proved that the inventive method is applicable to other chemokines, too. Specifically C-terminal fusion of a CXC-based decoy protein, IL-8, to human serum albumin improved the in vivo parameters and chemokine displacement pattern and its oligomerization behavior compared to the unfused decoy protein. One novel fusion decoy protein developed according to the inventive methods with high therapeutic value was called ATG03.

The GAG-binding fusion proteins according to the present invention can also be formulated as a pharmaceutical composition comprising the mutant GAG binding fusion protein or a polynucleic acid molecule coding for GAG binding fusion protein, a vector containing an isolated DNA molecule coding for the GAG binding fusion protein, and a pharmaceutically acceptable carrier.

Said GAG-binding fusion protein or the polynucleotide coding therefore or the vector containing said polynucleotide can also be used for inhibiting or suppressing the biological activity of the respective wild type protein.

The inventive GAG-binding fusion protein according to the invention can also be used in a method for preparing a medicament.

According to a specific embodiment of the invention, the inventive fusion protein can be used, but is not limited to, for the prevention or treatment of oncological indications (including metastasis), multiple scelerosis, myocardiac infarction, restenosis, fibrotic disorders (including IPF), non-alcoholic steatohepatitis, type 2 diabetes and associated co-morbidities, lupus nephritis, inflammatory diseases, chronic obstructive pulmonary disease (COPD), cystic fibrosis (CF), solid organ transplantation, delayed graft function, uveitis, psoriasis, and arthritis.

FIGURES

FIGS. 1A-1C: Sequences of wild type MCP-1 and IL-8 and MCP-1 (ATG01, ATG02) and IL-8 (ATG03) mutants and the respective HSA sequence. Mutations with respect to the wild type chemokine are underlined, modification in the wild-type HSA sequence is bold.

FIG. 2: Binding isotherm of MCP-1 mutant protein ATG01 for low molecular weight heparin, the prototypic GAG, as ligand. The Kd value for this interaction was determined by Biacore to be 345 nM.

Figure 3A:
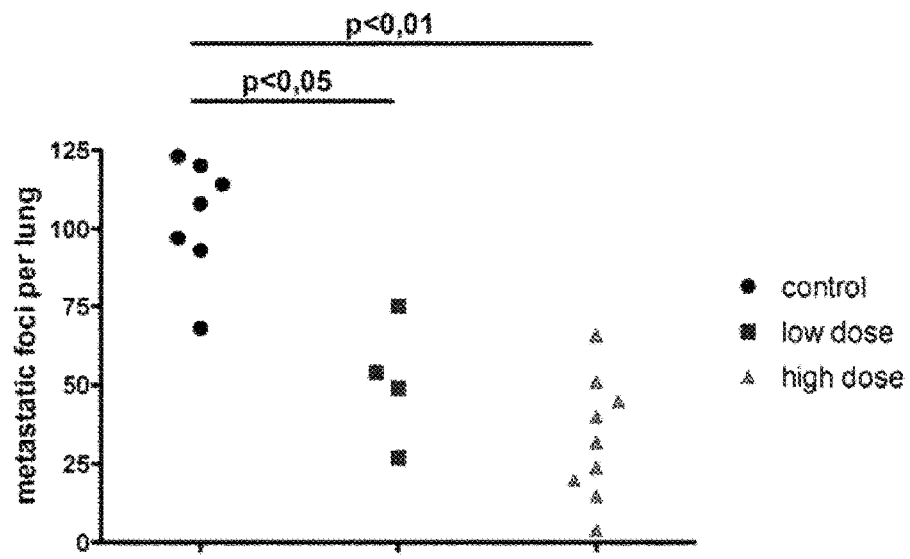
Figure 3B:
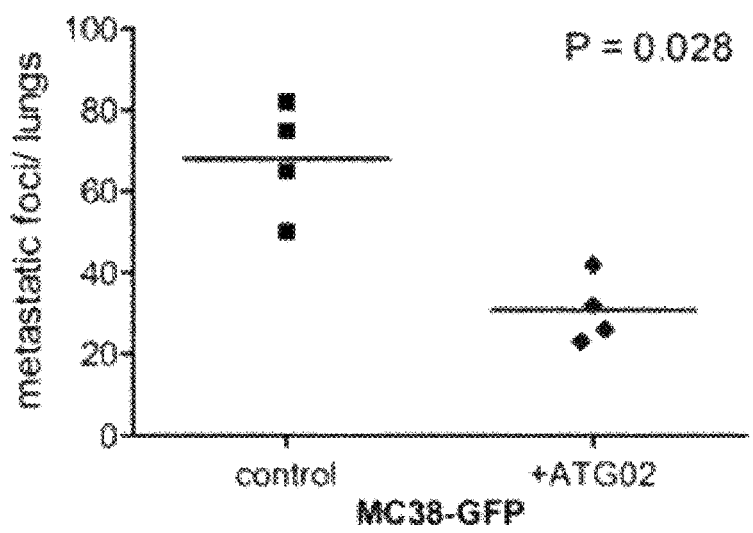

FIG. 3: Experimental metastasis. $3 \times 10^5$ MC-38GFP cells were injected into the tail vein. A) Treated mice received 10 minutes earlier and 24 hours later either 200 μg (low dose) or 800 μg (high dose) of ATG01. Four weeks later, lungs were perfused with PBS and the number of metastatic foci was determined. B) Treated mice received 10 minutes earlier 800 μg of ATG02.

Figure 4:
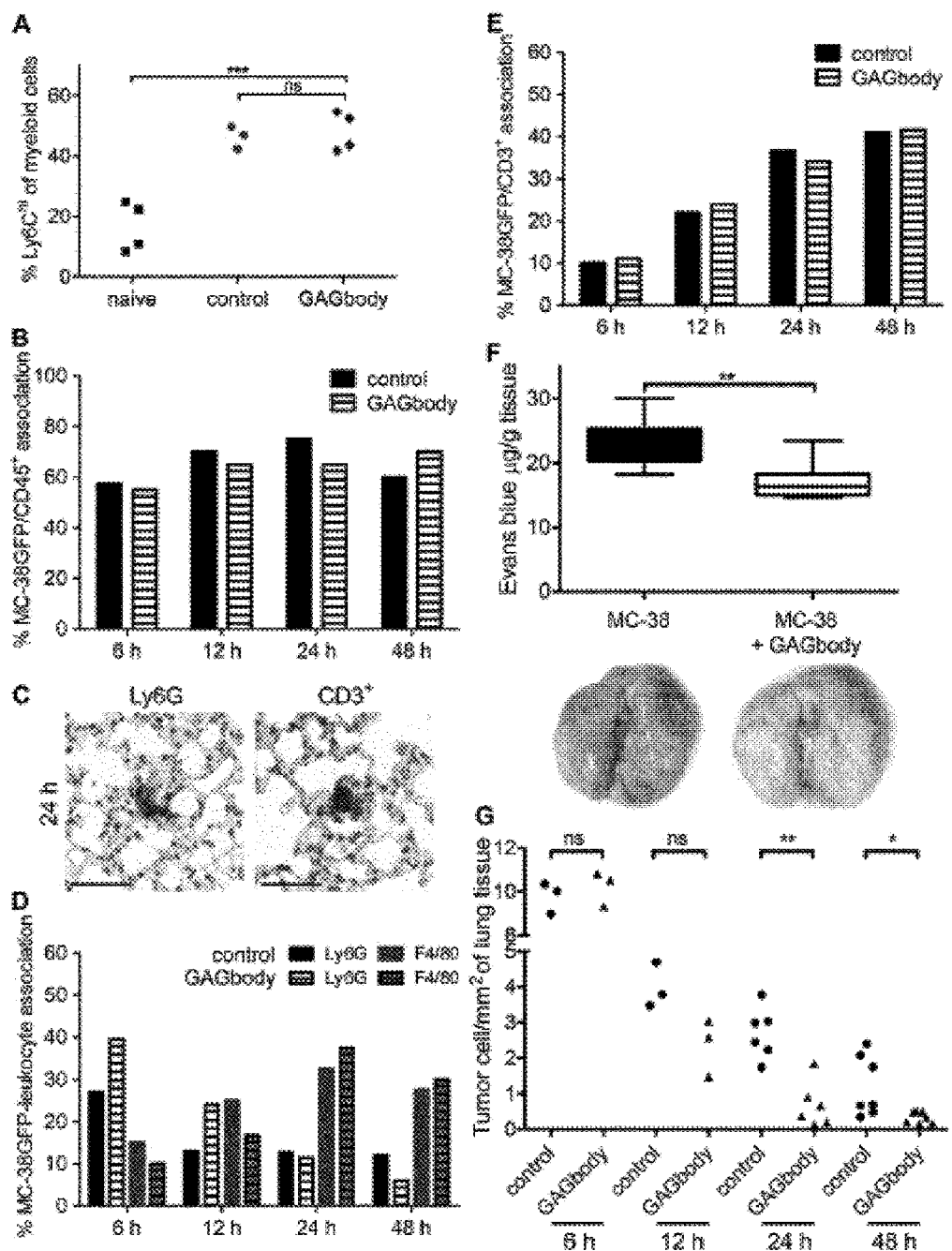

FIG. 4: Lung analysis of mice intravenously injected with MC-38GFP cells with or without ATG01 (GAGbody) treatment. A) Flow cytometry analysis of myeloid cells in circulation after two treatments (0 h and 24 h) with GAGbody (200 μg) analyzed 16 h after the last treatment. B) Flow cytometry analysis of myeloid cells in the lungs of MC-38GFP injected mice treated with GAGbody or controls (untreated) after 12 h compared to naïve lungs (no tumor cell injection). C-F) Histological analysis of tumor cell-leukocyte association from MC-38GFP-injected mice. Serial sections were evaluated for co-localization of $CD45^+$ cells (C), $Ly6G^+$, $F4/80^+$ cells (D) and $CD3^+$ cells (E) with tumor cells. F) Representative images of $Ly6G^+$- and $CD3^+$-MC-38GFP association; leukocytes (light), MC-38GFP=(dark); bar=50 μm. (n≥40 tumors in lungs analyzed). G) Vascular permeability determination. Evans blue extracted from mouse lungs was normalized to the lung weight (n=6). Representative macroscopic images are shown. Statistics: two-tailed Student's t-test.; **, P<0.01. H). Tumor cell seeding in the lungs of mice 6 h, 12 h, 24 h and 48 h after intravenous injection of MC-38GFP cells evaluated by immunohistochemistry. GAGbody was injected at the time of tumor cell injection only. Mice without GAGbody injection (control) were used as controls.

Figure 5:
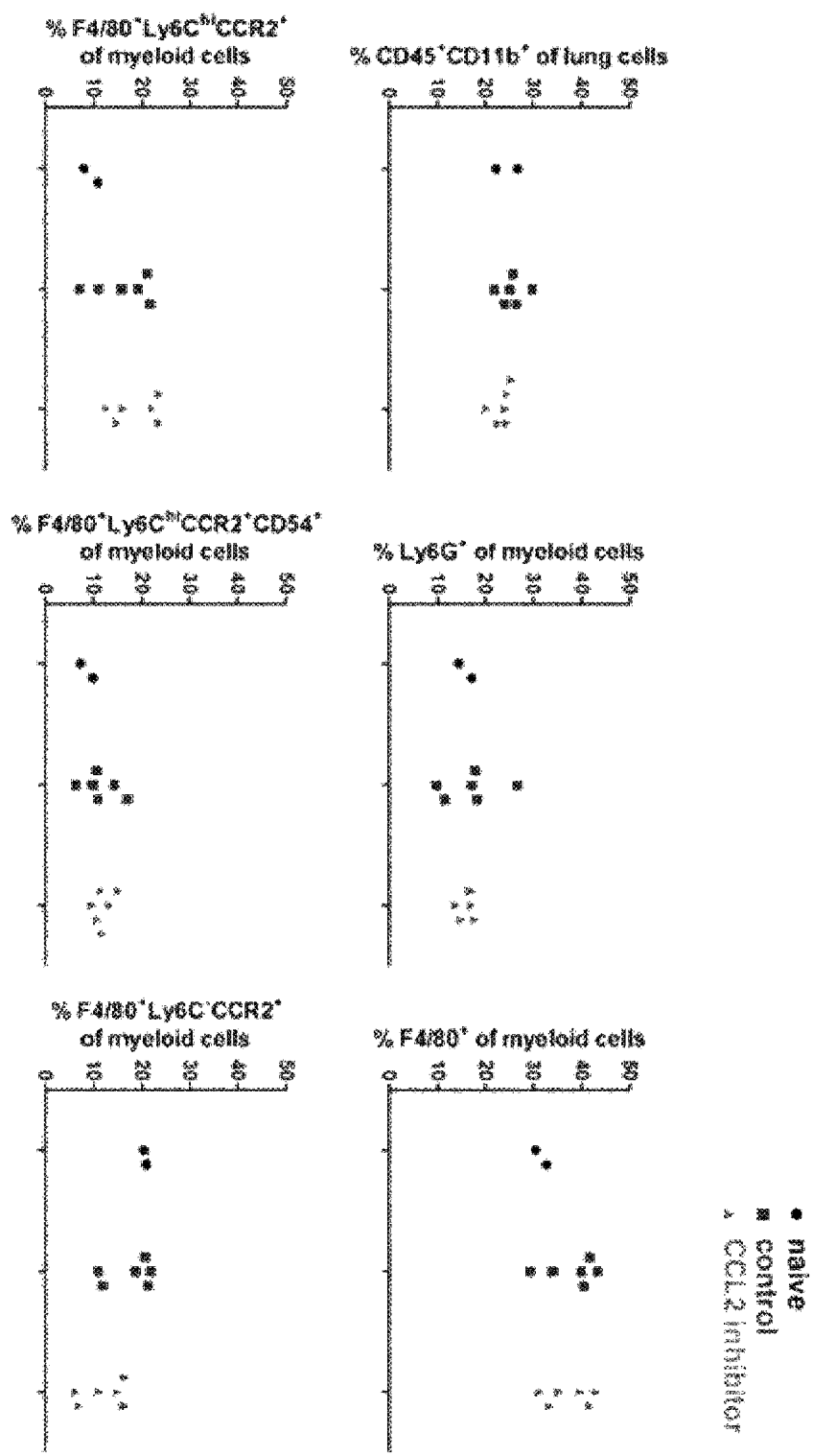

FIG. 5: Myeloid recruitment. $3 \times 10^5$ MC-38GFP cells were injected into the tail vein. Treated mice received 10 minutes earlier 800 μg of ATG01 (CCL2 inhibitor). 24 hours later lungs were perfused, enzymatically digested and the single cell suspensions were further processed for FACS analysis. (dots: naïve, squares: control; triangles: CCL2 inhibitor)

Figure 6:
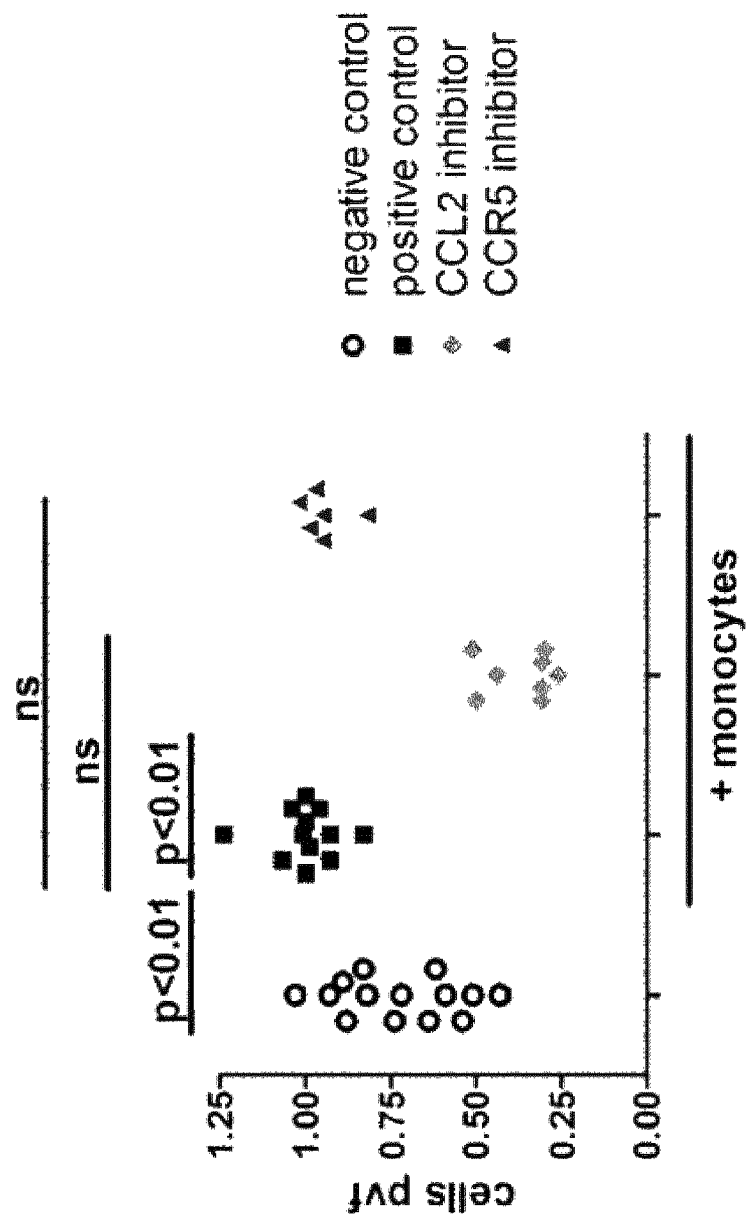

FIG. 6: Inhibition of cancer cell transmigration (in vitro). The transmigration efficiency of murine colon carcinoma cells (MC-38GFP) in presence of primary monocytes across a layer of primary lung vascular endothelial cells was tested in presence of indicated inhibitors for 16 hours (CCL2 inhibitor: ATG01). The relative number of transmigrated MC-38GFP cells per view field (pvf) was counted.

Figure 7A:
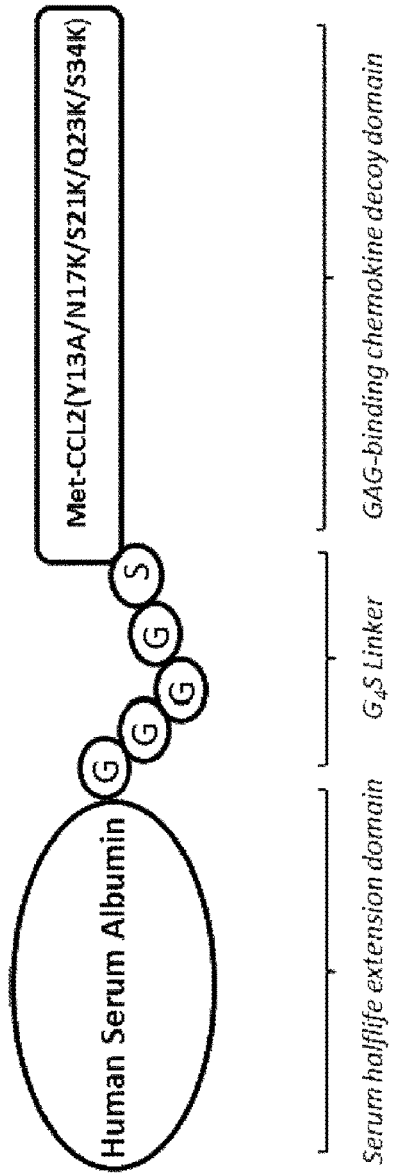
Figure 7B:
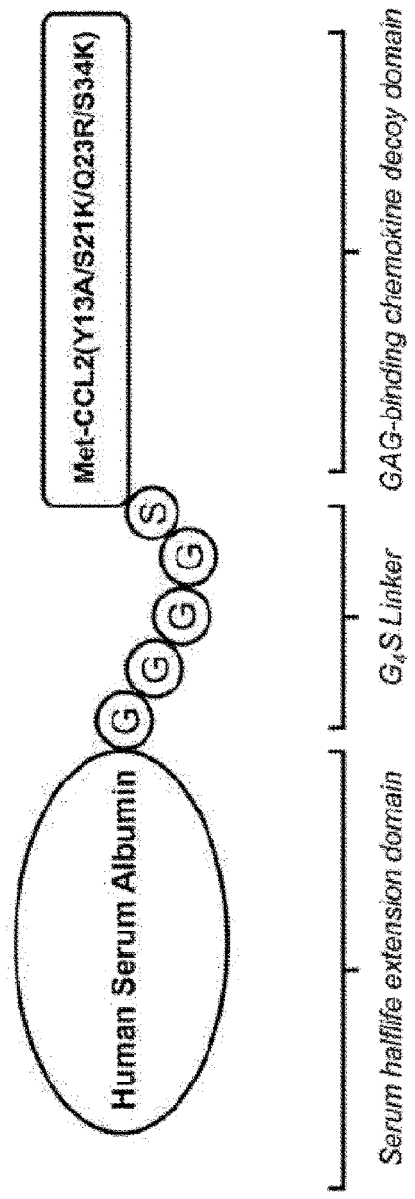

FIGS. 7A and 7B: Schematic structure of MCP-1 fusion proteins. FIG. 7A is a description of the MCP-1 fusion protein with human serum albumin; FIG. 7B is a description of the ATG01 fusion protein with human serum albumin FIG. 8: Pharmacokinetic profile to determine the serum half life and bioavailability of dnCCL2 and GAGbody in vivo. Mice were intravenously injected with dnCCL2 (200 μg/kg) and GAGbody (200 μg/kg dnCCL2 equivalent), and the serum level of each protein was determined at different time-points. n=3.

Figure 9:
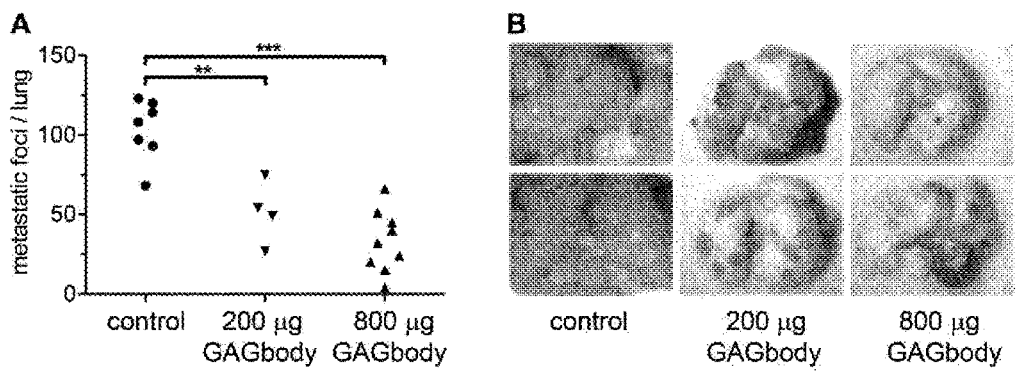

FIG. 9: GAGbody (ATG01) reduces experimental metastasis. A) Mice were intravenously injected with GAGbody (17.5 μmol=200 μg or 70 μmol=800 μg); HSA (17.5 μmol=200 μg) or dnCCL2 (70 μmol=200 μg) 10 minutes before and 24 h after MC-38GFP cell application. Metastatic foci were quantified after 28 days. , P<0.01; *, P<0.001. B) Representative macroscopic images of perfused lungs from control and GAGbody treated mice. Mice were intravenously injected with GAGbody (70 μmol=800 μg) 10 minutes before and 24 h after 3LL cell application. Metastatic foci were quantified after 12 days.

Figure 10:
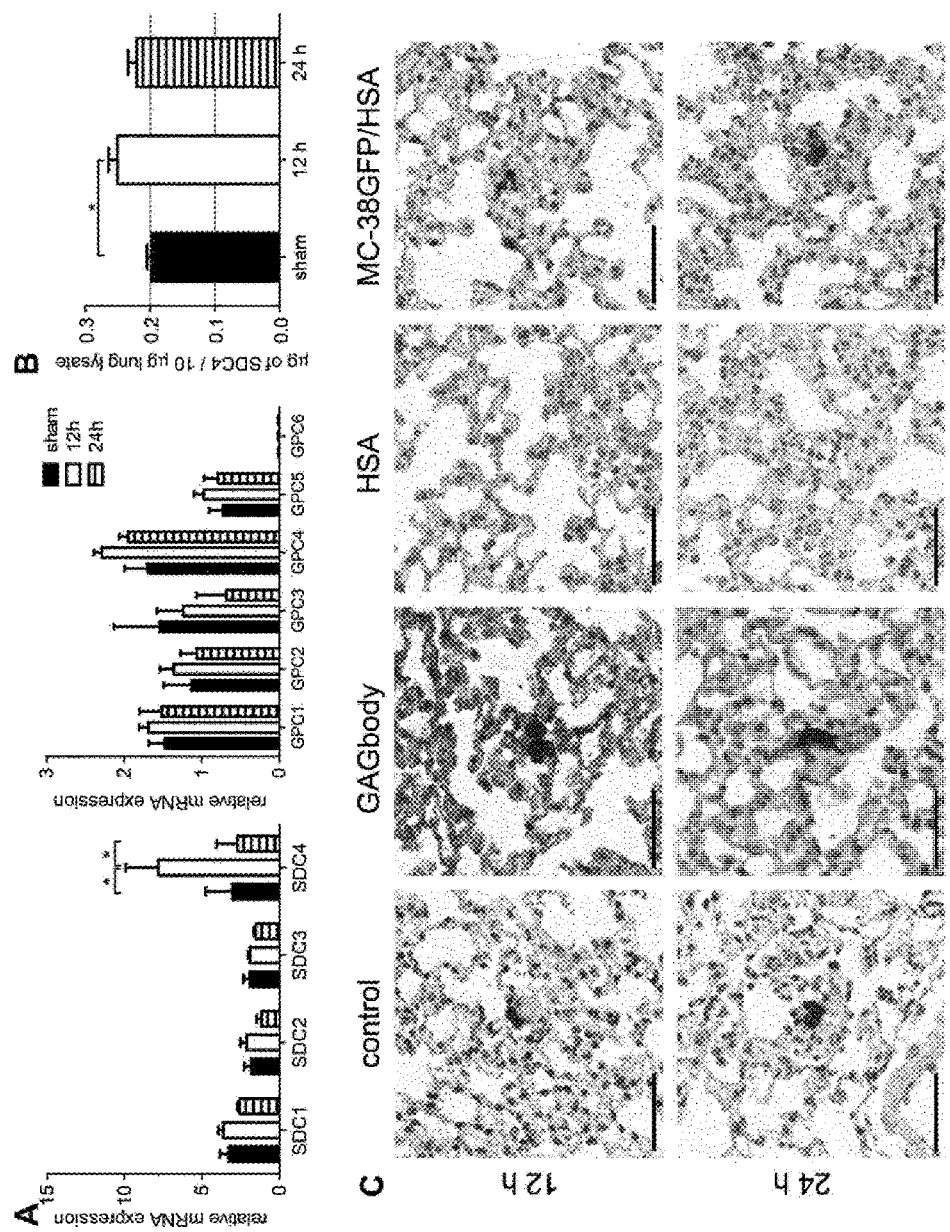

FIG. 10: Increased SDC4 expression around tumor cells correlates with the enhanced presence of GAGbody (ATG01) in the lung vasculature. A) Proteoglycan expression in the lungs of mice 12 h and 24 h after MC-38GFP injection compared to sham treated mice. Relative mRNA expression levels of syndecan 1,2,3,4 and glypicans 1,2,3, 4,5,6 compared to GAPDH expression. n≥3, *=p<0.05. B) Quantification of a dot-blot analysis of syndecan-4. Lung lysates of mice 12 h and 24 h after MC-38GFP injection were compared to sham control (non-injected lungs). *=p<0.05. C) Relative mRNA expression of SDC4 in endothelial cells purified from lungs of a naïve and MC-38GFP injected after 12 h, respectively; was normalized to GAPDH expression. *=p<0.05. Syndecan-4 detection was performed in lungs of a naïve and MC-38GFP injected after 12 h. Bar=20 µm. GAGbody staining (brown) of lungs from MC-38GFP (red) injected mice after 12 h and 24 h using HSA antibody. Lungs of mice injected: only with MC-38GFP (control); with GAGbody and MC-38GFP cells (GAGbody), with HSA only (HSA); and with HSA and MC-38GFP (MC-38GFP/HSA). Black arrowheads indicate the specific GAGbody staining around a tumor cell. Bar=50 µm.

Figure 11:
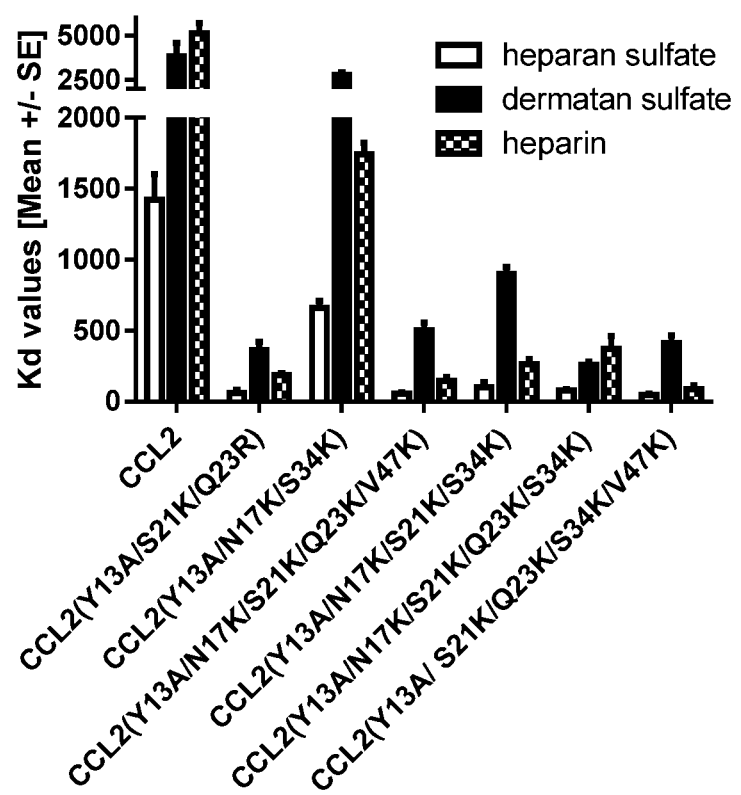

FIG. 11: Binding constants of CCL2, CCL2(Y13A/S21k/Q23R), CCL2(Y13A/N17K/S34K), CCL2(Y13A/N17K/S21K/Q23K/V47K), CCL2(Y13A/N17K/S21K/S34K), CCL2(Y13A/N17K/S21K/Q23K/S34K), CCL2(Y13A/S21K/Q23K/S34K/V47K) with heparan sulphate, dermatan sulphate and heparin. The data represents mean values+Stdev of three independent measurements.

Figure 12:
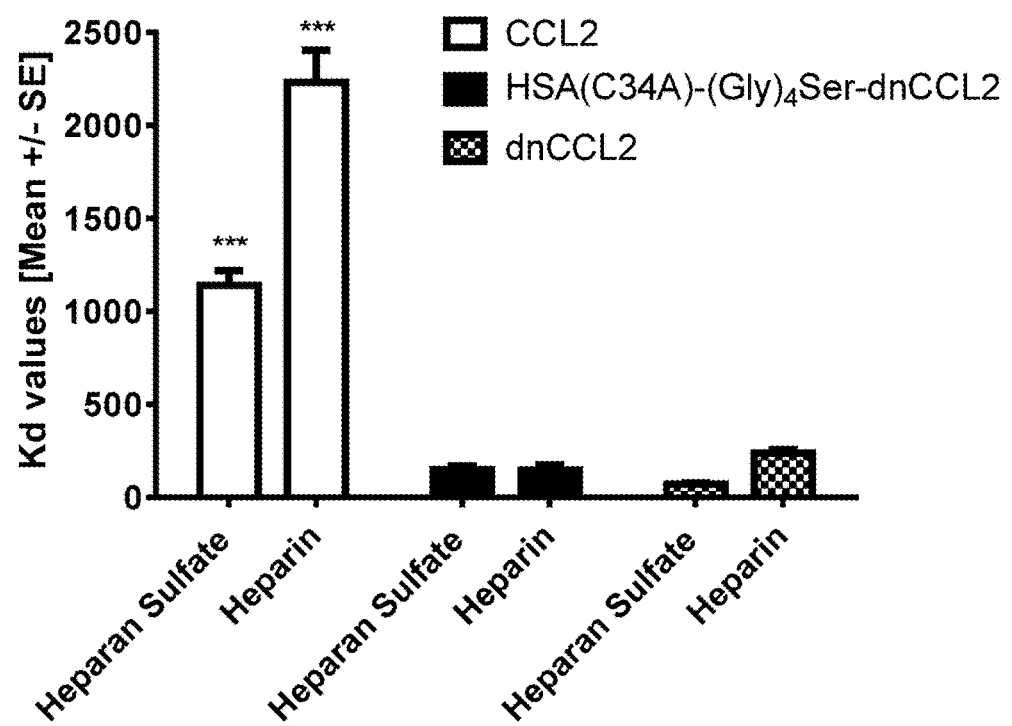

FIG. 12: Binding isotherms of CCL2, dnCCL2, and HSA(C34A)-(Gly)$_4$Ser-dnCCL2 with heparan sulfate and heparin. Data are shown as means+Stdev, *p<0.05 was considered as statistically significant.

Figure 13:
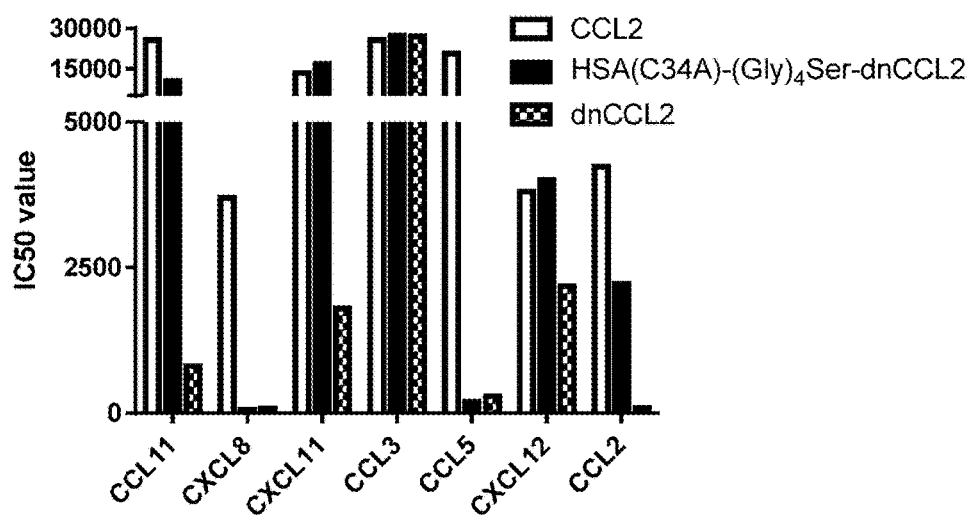

FIG. 13: Displacement profile of CCL2, dnCCL2 and HSA(C34A)-(Gly)$_4$Ser-dnCCL2 for 7 different chemokines on heparan sulfate.

Figure 14:
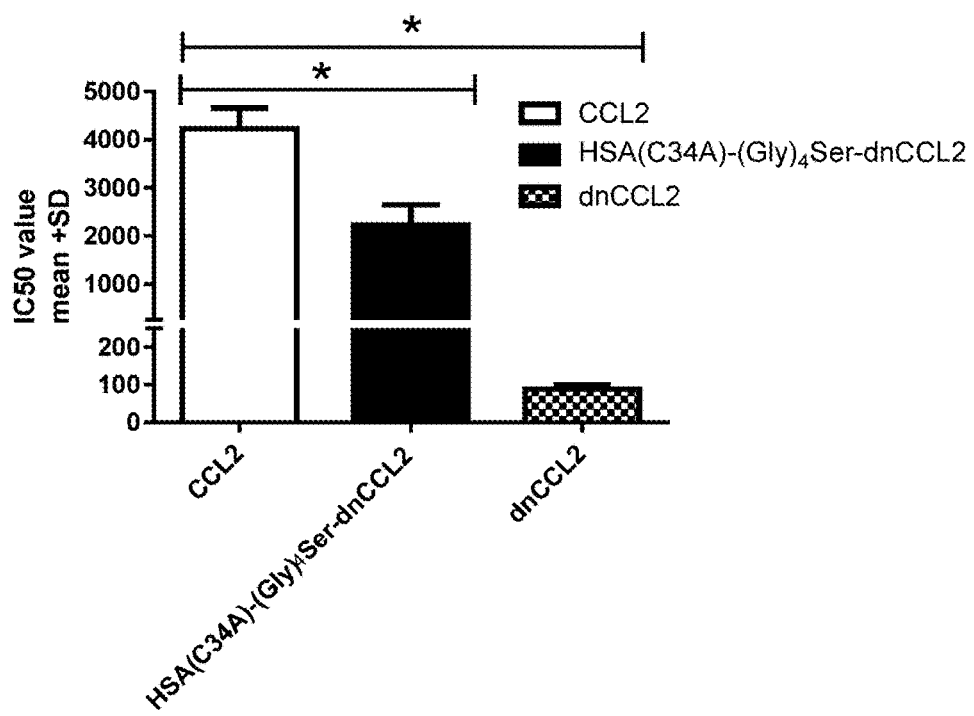

FIG. 14: Enlarged displacement profile for CCL2 on heparan sulfate. Data are shown as means+stdev, *p<0.05 was considered as statistically significant.

Figure 15:
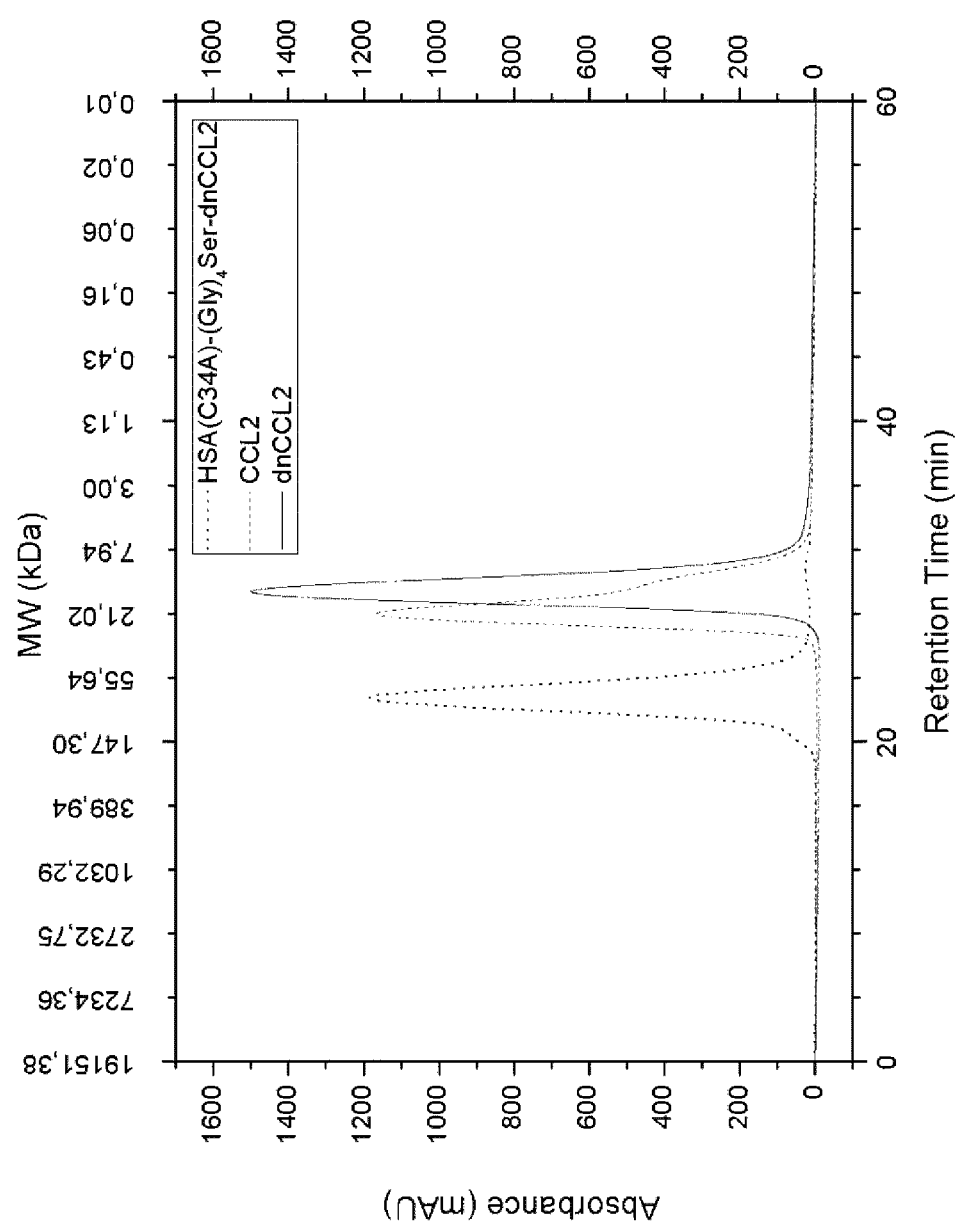

FIG. 15: Size exclusion chromatography of CCL2, dnCCL2, and HSA(C34A)-(Gly)$_4$Ser-dnCCL2.

Figure 16:
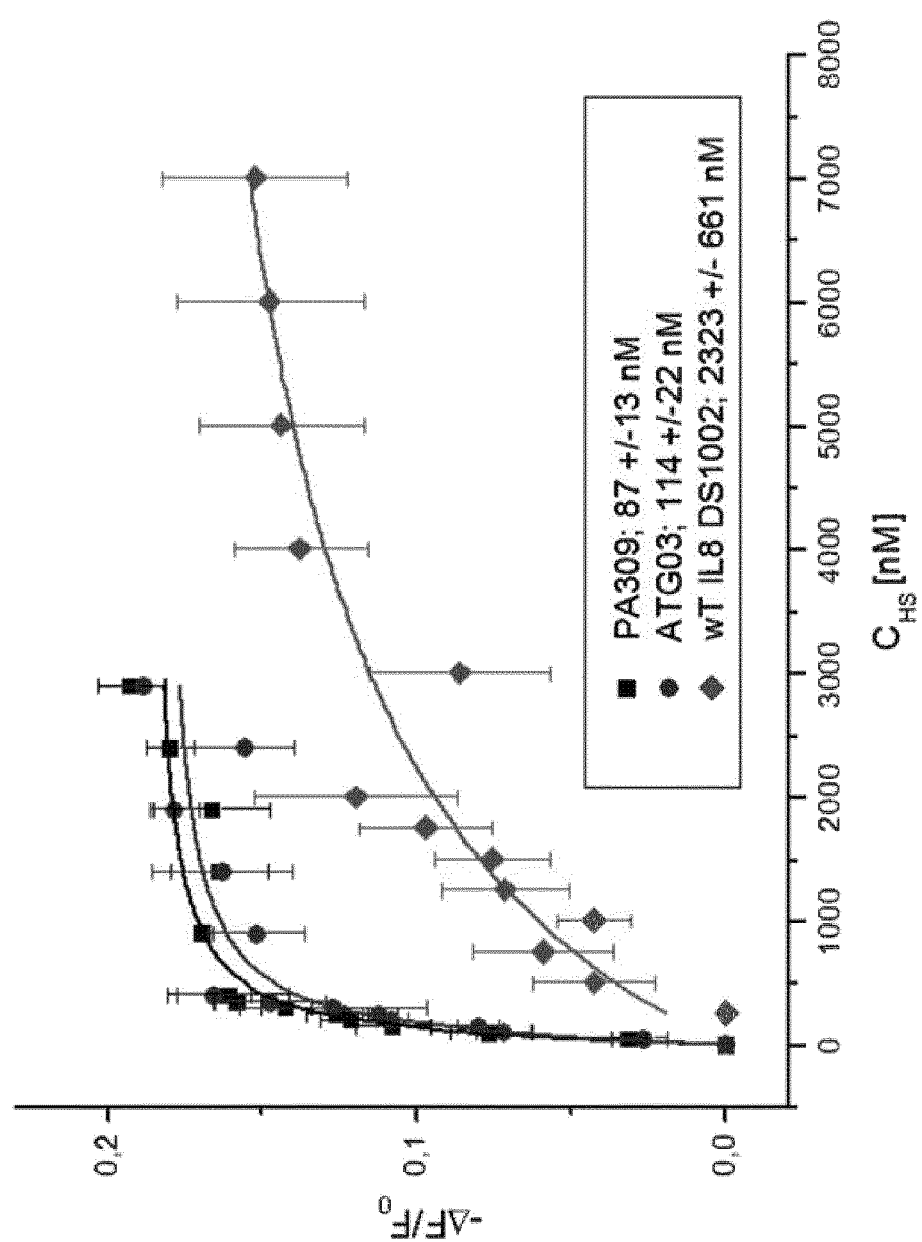

FIG. 16: Binding isotherms of wtIL-8, the unfused IL-8 mutant (PA309) and ATG03.

DETAILED DESCRIPTION OF THE INVENTION

The present invention provides a novel, monomeric fusion protein with increased GAG binding affinity and reduced G-protein coupled receptor (GPCR) activity compared to wild type protein due to modifications within the GAG binding and GPCR binding regions, linked to human serum albumin sequence and optionally containing a linker sequence between the protein and HSA.

According to the embodiment of the invention, the fusion protein comprises
a) a GAG binding protein with increased GAG binding affinity and reduced G-protein coupled receptor (GPCR) activity compared to the respective wild type protein, comprising a modification in a structure-conserving way by replacement of at least two amino acids by basic and/or electron donating amino acids in the GAG binding region and/or in the vicinity thereof and a modification of the GPCR binding region
b) a human serum albumin (HSA) sequence and optionally
c) a linker sequence between said HSA sequence and said GAG binding protein.

According to an embodiment of the invention, the monomeric protein of the invention can be, but are not limited to chemokines, cytokines or growth factors, for example said proteins may be chemokines but are not limited to CXC, CC, CX3C or XC, specifically MCP-1, IL-8, RANTES, SDF-1 or growth factor proteins like VEGF, EGF, HGF or GMCSF or functional fragments thereof.

The term "functional fragment" as used herein shall refer to any fragment or derivative or part of a polypeptide or protein moiety that has increased GAG binding affinity with respect to the GAG binding affinity of the respective wild type protein.

The functional fragments may further have a receptor binding region with an activity that is at least 50%, preferably at least 75%, preferably at least 90% of the receptor binding activity of the respective full length protein.

According to a specific embodiment of the invention, the GAG-binding fusion protein is HSA-linker-MCP-1.

According to a specific embodiment of the invention, the GAG-binding fusion protein is HSA-linker-IL-8.

The HSA sequence can comprise the wild type sequence or 90%, specifically at least 95%, more specifically at least 99%, more specifically at least 99.9% sequence identity with the wild type sequence (SEQ ID No. 6).

According to a further embodiment, the HSA sequence comprises an amino acid modification at amino acid position 34 according to the numbering of SEQ ID No. 4 which prevents inter- and intra-molecular disulfide bridge formation. More specifically, the amino acid C is substituted by A.

According an embodiment the HSA sequence comprises SEQ ID No. 4 or comprises at least 90%, preferably at least 95%, preferably at least 99% of SEQ ID No. 4.

According to a further embodiment, the HSA sequence consists of SEQ ID No. 4.

The HSA sequence and the protein moiety of the inventive monomeric fusion protein can be fused together either directly or via a linker sequence of at least two amino acids, specifically of at least three, at least four, at least five, at least six, at least seven, at least eight, at least nine or at least ten or more than ten amino acids.

According to an alternative embodiment, the linker sequence is of two amino acids, specifically of 3, 4, 5, 6, 7, 8, 9, 10, 11, 12, 15, 14, 15 amino acids.

Specifically, said HSA sequence is linked to the C-terminus of the protein.

Said linker proteins shall not have any unspecific glycan binding and are not immunogenic. Preferably, the linker sequences are flexible.

Specifically, the linker sequence comprises an amino acid sequence GGGGS (SEQ ID No. 5) or repeated sequences thereof.

However, any other linker sequence may be tested by the skilled person in view of chemokine and/or growth factor binding/activation.

According to the invention, the monomeric fusion protein shows increased bioavailability specifically due to increased serum half-life.

According to the invention the term "bioavailability" refers to the fraction of an administered dose of unchanged drug that reaches the systemic circulation, one of the principal pharmacokinetic properties of drugs. When a medication is administered intravenously, its bioavailability is 100%. When a medication is administered via other routes (such as oral), its bioavailability generally decreases due to incomplete absorption and first-pass metabolism or may vary from patient to patient. Bioavailability is meant a term that indicates measurement of total amount of drug that reaches the general circulation from an administered pharmaceutical composition, e.g. from an orally or intravenously administered pharmaceutical composition, in a single dose or multiple dose setting. It is often expressed in %, i.e. area under the concentration time curve "AUC" (from 0 time to infinity) or AUC (from o time to 48 or 72 h) of a single dose of the drug when administered e.g. orally, in serum, blood or plasma compared to the AUC (from 0 time to infinity) or AUC (from o time to 48 or 72 h) of single dose of the same amount of drug when injected, i.e. AUC(orally)/AUC(injected) expressed in %.

According to the invention, the monomeric fusion protein is selectively competitive which means that the fusion protein displaces in a standardized set-up as few other GAG-binding proteins as possible from a target GAG structure, preferably only the respective wild type.

According to a further embodiment, the proteins are monomeric proteins, thus there is no oligomerization of protein moieties. This is highly advantageous, because multimerisation could lead to unwanted side effects due to a broader GAG-binding protein displacement profile (see above). In addition, larger aggregates of GAG-binding proteins exhibit commonly a lower GAG-binding affinity, compared to the monomeric protein, thus leading to lower bio-activity.

According to a further embodiment, the monomeric MCP-1 mutant comprises an amino acid sequence wherein at least two amino acids at positions 17, 21, 23, 34 and/or 47 according to the numbering of SEQ ID No. 1 are modified. Specifically preferred are MCP-1 mutants comprising amino acid substitutions at positions 17, 21, 23 and/or 34.

According to a further embodiment, the monomeric IL-8 mutant comprises an amino acid sequence wherein at least two amino acids at positions 17, 21, 70 and/or 71 according to the numbering of SEQ ID No. 7 are modified.

According to a further embodiment, the basic amino acids are selected from the group consisting of arginine (R), lysine (K) and histidine (H) and the electron donating amino acids are selected from the group consisting of asparagine (N) or glutamine (Q).

According to a specific embodiment, Y at position 13 of the MCP-1 mutant protein is substituted by alanine to prevent CCR2 binding.

Y13 and R18 were shown to be also critical residues for signaling, and the replacement of these residues by other amino acid residues gave rise to a protein unable to induce chemotaxis. Two-dimensional 1H-15N HSQC spectra recorded on both deletion and substitution MCP-1 variants revealed that these mutations do not generate misfolded proteins (Chad D. Paavola et al., J. Biol. Chem., 273 (50), 33157-33165 (1998)).

In a further embodiment, the GAG binding fusion protein contains an N-terminal methionine to inhibit CCR2 binding. The N-terminal methionine reduces the binding affinity of MCP-1 for CCR2 on THP-1 cells (Hemmerich S. et al, Biochemistry 38 (40), 13013-13025 (1999)) so that the chemotactic potency of [Met]-MCP-1 is approximately 300-fold lower than of the wild type (Jarnagin K. et al., Biochemistry 38, 16167-16177 (1999)).

According to the definition as used in the present application the term MCP-1 mutant protein can also include any parts or fragments thereof that still show chemokine-like fold but impacts on/knocks out chemokine activity like monocyte or T-cell chemotaxis and Ca-release.

The term "vicinity" as defined according to the invention comprises amino acid residues which are located within the conformational neighbourhood of the GAG binding site but not positioned at the GAG binding sites. Conformational neighbourhood can be defined as either amino acid residues which are located adjacent to GAG binding amino acid residues in the amino acid sequence of a protein or amino acids which are conformationally adjacent due to three dimensional structure or folding of the protein.

The term "adjacent" according to the invention is defined as lying within the cut-off radius of the respective amino acid residues to be modified of not more than 20 nm, preferably 15 nm, preferably 10 nm, preferably 5 nm.

According to the invention, the term "GAG binding region" for amin acid substitutions also encompasses amino acid modifications adjacent to said GAG binding region.

To be able to perform their biological function, proteins fold into one, or more, specific spatial conformations, driven by a number of noncovalent interactions such as hydrogen bonding, ionic interactions, Van der Waals' forces and hydrophobic packing. Three dimensional structures can be determined by known methods like X-ray crystallography or NMR spectroscopy.

Identification of native GAG binding sites can be determined by mutagenesis experiments. GAG binding sites of proteins are characterized by basic residues located at the surface of the proteins. To test whether these regions define a GAG binding site, these basic amino acid residues can be mutagenized and decrease of heparin binding affinity can be measured. This can be performed by any affinity measurement techniques as known in the art.

Rational designed mutagenesis by insertion or substitution of basic or electron-donating amino acids can be performed to introduce foreign amino acids in the vicinity of the native GAG binding sites which can result in an increased size of the GAG binding site and in an increase of GAG binding affinity. The size can be increased by at least one additional amino acid introduced into the MCP-1 protein, specifically by introduction of at least two amino acids, more specifically of at least three amino acids.

A deviation of the modified structure as measured by far-UV CD spectroscopy from wild type MCP-1 structure of less than 30%, preferably less than 20%, preferably less than 10% is defined as structure conserving modification according to the invention.

According to an alternative embodiment, the structure conserving modification is not located within the N-terminus of the MCP1 protein.

The inventive MCP-1 protein can comprise any combinations of amino acid modifications at positions N17, S21, Q23 and S34 resulting in an MCP-1 mutant protein having increased GAG binding compared to wt MCP-1.

The amino acid sequence of the modified MCP-1 molecule can be described by the general formula:

(SEQ ID No. 9)
DAHKSEVAHRFKDLGEENFKALVLIAFAQYLQQAPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK

```
-continued
EFNAETFTFHADICTLSEKERQIKKQTALVELVKHKPKATKEQLKAVMDD

FAAFVEKCCKADDKETCFAEEGKKLVAASQAALGL(X1)m(M)nQPDAINA

PVTCCAQFT(X2)RKI(X3)V(X4)RLASYRRITS(X5)KCPKEAVIFKT

IVAKEICADPKQKWVQDSMDHLDKQTQTPKT
``` wherein X1 is selected from the group consisting of G and/or S, preferably it is of sequence GGGGS, wherein X2 is selected from the group consisting of N, R, K, H or Q, preferably it is K, wherein X3 is selected from the group consisting of S, K, H, N and/or Q, preferably it is K, wherein X4 is selected from the group consisting of R, K, H, N and/or Q, preferably it is K, wherein X5 is selected from the group consisting of S, K, H, N and/or Q, preferably it is K, and wherein m can be any of 0, 1, 2, 3 or 4 and n can be 0 or 1.

According to a specific embodiment, a monomeric fusion protein is covered which is of the structure HSA GGGS Met-MCP-1 Y13A N17K S21K Q23K S34K, V47K, HSA GGGS Met-MCP-1 Y13A N17K S21K Q23K S34K, HSA GGGS Met-MCP-1 Y13A S21K Q23K S34K, HSA GGGS Met-MCP-1 Y13A S21K Q23K S34K.

The amino acid sequence of the modified IL-8 molecule can be described by the general formula:

```
                                              (SEQ ID No. 10)
DAHKSEVAHRFKDLGEENFKALVLIAFAQYLQQAPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK

EFNAETFTFHADICTLSEKERQIKKQTALVELVKHKPKATKEQLKAVMDD

FAAFVEKCCKADDKETCFAEEGKKLVAASQAALGL(X1)CQCIKTYSKP (X2)HPK(X3)IKELRVIES GPHCANTEIIVKLSDGRELC LDPKENWVQ

R VVEKFLKRA(X4)(X5)S
``` wherein X1 is selected from the group consisting of G and/or S, preferably it is of sequence GGGGS, wherein X2 is selected of the group consisting of R, K, H, N and/or Q, preferably it is R, wherein X3 is selected of the group consisting of R, K, H, N and/or Q, wherein X4 is selected of the group consisting of R, K, H, N and/or Q, preferably it is K, and wherein X5 is selected of the group consisting of R, K, H, N and/or Q, preferably it is K.

According to an embodiment, the fused monomeric IL-8 the GPCR binding region is deleted. The IL-8 GPCR region is located within the first 10 N-terminal amino acids. The first N-terminal amino acids are involved in leukocyte activation, whereby in particular Glu-4, Leu-5 and Arg-6 were identified to be essential for receptor binding and activation. Therefore, either these three or even up to the first 10 N-terminal amino acids can be substituted or deleted in order to inhibit or down-regulate the receptor binding and activation.

For example, the fusion IL-8 protein can have the first 6 N-terminal amino acids deleted. As mentioned above, this mutant will not or to a lesser extent bind and activate leukocytes and/or promote neutrophil activation, so that it is particularly suitable for the treatment of organ transplant rejection.

Preferably, the modified IL-8 is selected from the group consisting of HSA-GGGGS-del6F17RE70KN71R, HSA-GGGGS-del6F17RE70RN71K, HSA-GGGGS-del6E70KN71K, HSA-GGGGS-del6F17RE70RN71K, and HSA-GGGGS-del6F17KF21KE70KN71K.

A further aspect of the present invention is an isolated polynucleic acid molecule which codes for the inventive protein as described above.

The polynucleic acid may be DNA or RNA. Thereby the modifications which lead to the inventive MCP-1 mutant protein are carried out on DNA or RNA level. This inventive isolated polynucleic acid molecule is suitable for diagnostic methods as well as gene therapy and the production of inventive MCP-1 mutant protein on a large scale.

A further aspect relates to a vector comprising an isolated DNA molecule according to the present invention, as defined above. The vector comprises all regulatory elements necessary for efficient transfection as well as efficient expression of proteins. Such vectors are well known in the art and any suitable vector can be selected for this purpose.

A further aspect of the present invention relates to a recombinant cell, specifically a non-human cell which is transfected with an inventive vector as described above. Transfection of cells and cultivation of recombinant cells can be performed as well known in the art. Such a recombinant cell as well as any descendant cell therefrom comprises the vector. Thereby, a cell line is provided which expresses the fusion GAG binding protein either continuously or upon activation depending on the vector.

A further aspect of the invention relates to a pharmaceutical composition comprising a monomeric fusion GAG binding protein of the invention, a polynucleic acid or a vector according to the present invention, as defined above, and a pharmaceutically acceptable carrier. Of course, the pharmaceutical composition may further comprise additional substances which are usually present in pharmaceutical compositions, such as salts, buffers, emulgators, coloring agents, etc.

The pharmaceutical composition can be administered by any route as known in the art, specifically by oral, subcutaneous, intramuscular administration or by inhalation.

A further aspect of the present invention relates to the use of the inventive fusion GAG binding protein, a polynucleic acid or a vector according to the present invention, as defined above, in a method for either in vivo or in vitro inhibiting or suppressing the biological activity of the respective wild type protein.

The modified GAG binding mutant protein of the invention will act as an antagonist whereby the side effects which occur with known recombinant proteins will not occur with the inventive fusion GAG binding mutant protein. In this case this will particularly be the biological activity involved in oncological indications (including metastasis), multiple sclerosis, myocardiac infarction, restenosis, fibrotic disorders (including IPF), non-alcoholic steatohepatitis, type 2 diabetes and associated co-morbidities, and lupus nephritis.

The MCP-1 mutant protein of the invention is a CCL2-based decoy protein with improved GAG-binding affinity which was shown to successfully prevent tumor cell transmigration, reduces pulmonary metastatic burden, educes tumor induced vascular permeability and does not interfere with myeloid cell recruitment Therefore, a further use of the inventive fusion GAG binding protein, a polynucleic acid or a vector according to the present invention, as defined above, is in a method for producing a medicament for the treatment of cancer disease and the prevention or treatment of tumor metastasis. In particular, it will act as antagonist without or with reduced side effects and will be particularly suitable for the treatment of cancer related as well as macrophage/monocyte- and neutrophil-related inflammatory diseases.

Therefore, a further aspect of the present invention is also a method for the treatment of cancer diseases, wherein the inventive mutant protein according to the invention, the isolated polynucleic acid molecule or vector according to the present invention or a pharmaceutical preparation according to the invention is administered to a patient.

The following examples describe the invention in more detail without limiting the scope of the invention.

EXAMPLES

Example 1

Experimental Metastasis Model
In Vivo Experiment 1:
C57BL/6 mice were intravenously injected with $3 \times 10^5$ syngeneic mouse colon carcinoma MC-38GFP cells that were grown in DMEM medium with 10% FCS. Mice were treated with ATG01 (200 μg) was i.v. injected 10 min prior to i.v. injection of MC-38GFP cells. ATG01 was further applied intravenously at +24 h at 200 μg. Another group of mice were treated at the same protocol but with a 800 μg dose (high dose). Yet another group of mice was treated by the same protocol with 800 μg ATG02.

The data are shown in FIG. 3.

SUMMARY AND CONCLUSIONS

ATG01 and ATG02 are efficient inhibitors of CCL2-based metastatic seeding. Two doses of ATG01 (200 μg) are enough to attenuate metastatic seeding.

Phase I (Experimental Metastasis Model)
1) In vitro analysis of ATG01 ability to block CCL2-mediated tumor cell transmigration.

To test ATG01 anti-metastatic activity we performed tumor cell transmigration in an in vitro assay that was shown to be dependent on CCR2-CCL2 signaling (Wolf et al. Cancer Cell 22: 91-105). Tumor cell (MC-38) transmigration depends on CCR2 expression by endothelial cells. The efficacy of ATG01 was compared to that of a commercially available CCR2-inhibitor.

At least three independent experiments (i.e. batches of purified ECs and monocytes) were performed.

Briefly, primary lung microvascular endothelial cells ($3 \times 10^4$) were cultured on gelatin coated 24-well transwell inserts (8 μm) until confluency (2 days). Tumor cells ($2 \times 10^4$) with or without monocytes ($1 \times 10^5$) were added in the top well and let migrated toward FCS gradient from 1% FCS/ RPMI in the upper chamber and 10% FCS/RPMI in the lower chamber for 16 h. Inhibitors were added as indicated in FIG. 1.

After 16 hrs of co-culture, the upper side of the insert was scraped off and the insert fixed in 1.5% paraformaldehyde. The transwell membrane was removed and mounted on a slide. Tumor cells on the lower side of the membrane as well as in the lower wells were analyzed with a fluorescence microscope (Zeiss) and tumor cells in the lower chamber were counted. Each point in the graph in FIG. 6 represents data from an individual assay.

Monocytes induced tumor cell transmigration across the endothelium. This process was significantly reduced to the background levels by ATG01 (100 μg/ml, FIG. 6). This reduction was comparable to treatment with a small molecular inhibitor of CCR2 RS 504393 (Tocris). ATG01 is an effective inhibitor of CCL2-CCR2 mediated transmigration across the endothelium that is a prerequisite for a successful metastasis.

Example 2

Experimental Procedures
Mice—
Animals were maintained under standard housing conditions and experiments were performed according to the guidelines of the Swiss Animal Protection Law, and approved by Veterinary Office of Kanton Zurich. C57BL/6 mice were purchased from the Jackson Laboratory. Animal care and handling procedures were performed in accordance with the European guidelines and all the experiments were conducted under conditions previously approved by the local animal ethics committee in Graz (FA10A-78Po-5/2011-5).

dnCCL2 and GAGbody (ATG01) definition—The unfused CCL2 mutant (Met-CCL2 Y13A N17K S21K Q23R S34K=dnCCL2) was produced in *E. coli* and characterized as previously described (Piccinini, A. M., et al., (2010) *J Biol Chem* 285, 8782-8792). The dnCCL2-based GAGbody was produced in *P. pastoris* and was purified by a 2-step downstream process. The expression, purification and characterization of this GAGbody are described in detail somewhere else (manuscript in preparation). In FIG. 7B the schematic structure of the GAGbody (ATG01) is shown.

Surface Plasmon Resonance (SPR)—
Binding of CCL2, GAGbody and dnCCL2 to unfractionated low molecular weight heparin (Iduron; Manchester, UK) was investigated on a BiacoreX100 system (GE Healthcare) as described earlier (Gerlza, T., et al., (2014). *Molecules* 19, 10618-10634). Briefly, measurements were performed under a steady PBS flow containing 0.005% Tween. Biotinylated heparin was coupled on a C1 sensor chip and each chemokine was measured at 7 different concentrations. Contact times for all injections and dissociations were 120 seconds at 30 μL/min over both Flow cells. Affinity constants were determined by a simple 1:1 equilibrium binding model, where Req is plotted against the analyte concentration. Data was fitted using the steady state formula that corresponds to the Langmuir adsorption equation, provided by the Biacore Evaluation Software.

Pharmacology of dnCCL2 and GAGbody—
057BL/6 male mice (Harlan, Italy), 6-8 weeks old, were intravenously injected with vehicle (PBS only), dnCCL2 (200 μg/kg body weight) or GAGbody (200 μg/kg body weight dnCCL2 equivalent) in the lateral tail vein. At defined time points serum was collected by heart puncture of deeply anesthetized mice (groups n=3). The concentration of dnCCL2 or GAGbody was analyzed using human MCAF ELISA kit (Hölzel, Germany). ELISA setup was performed according to the manufacturer's protocol.

In Vitro Transmigration Assay—

Primary pulmonary endothelial cells were isolated using a positive immuno-magnetic selection as described previously (Wolf, M. J., Hoos, A., Bauer, J., Boettcher, S., Knust, M., Weber, A., Simonavicius, N., Schneider, C., Lang, M., Sturzl, M., Croner, R. S., Konrad, A., Manz, M. G., Moch, H., Aguzzi, A., van Loo, G., Pasparakis, M., Prinz, M., Borsig, L., and Heikenwalder, M. (2012) *Cancer Cell* 22, 91-105). Briefly, lungs were perfused with PBS and digested with 1 mg/ml collagenase A (Roche, Basel, Switzerland), purified with anti-CD31 antibody (Life Technologies, Carlsbad, Calif.) coupled to anti-rat IgG MicroBeads (Miltenyi Biotec, Bergisch Gladbach, Germany). Primary lung microvascular endothelial cells ($3 \times 10^4$) were seeded on gelatin coated 24-well transwell inserts with 8 µm pores (BD, San Diego, Calif.) and allowed to grow to confluency (2 days). Tumor cells ($2 \times 10^4$) were seeded into transwell inserts with or without monocytes ($1 \times 10^5$) in 3% FCS/RPMI in the upper chamber and 10% FCS/RPMI in the lower chamber. The transmigration lasted for 16 h in presence or absence of 100 µg/ml dnCCL2, 10 µg/ml Maraviroc (R&D Systems, England), or 400 U/ml Tinzaparin (Leo Pharmaceuticals, Denmark). The number of transmigrated cells (MC-38GFP) was counted on the bottom of the insert membrane with a Zeiss AxioVision microscope (n=3-4).

Vascular Permeability Assay—

C57BL/6 mice were intravenously injected with $3 \times 10^5$ MC-38GFP cells with or without prior GAGbody (800 µg i.v.) treatment. Twenty four hours later 2 mg of Evans blue (Sigma Aldrich) were intravenously injected and lungs were perfused with PBS 30 min later as described previously (Wolf, M. J., Hoos, A., Bauer, J., Boettcher, S., Knust, M., Weber, A., Simonavicius, N., Schneider, C., Lang, M., Sturzl, M., Croner, R. S., Konrad, A., Manz, M. G., Moch, H., Aguzzi, A., van Loo, G., Pasparakis, M., Prinz, M., Borsig, L., and Heikenwalder, M. (2012) *Cancer Cell* 22, 91-105). Lungs were dissected, photographed and homogenized. Evans blue was extracted with formamide and the amount was measured with a spectrophotometer (absorbance at 620 nm).

Experimental Metastasis—

C57BL/6 mice were intravenously injected with $3 \times 10^5$ MC-38GFP or $1.5 \times 10^5$ 3LL cells, respectively. Mice were intravenously treated with indicated amount of GAGbody 10 minutes prior to tumor cell injection and 24 h post-tumor cell injection. Mice were euthanized 28 days later, lungs were photographed, the number of metastatic foci determined.

Statistics—

Statistical analysis was performed with the Graph Pad Prism software (version 5.0). All data are presented as mean±SEM and were analyzed by ANOVA with the post-hoc Bonferroni multiple comparison test, unless specified differently.

Results

Pharmacological Blocking of CCL2 Inhibits Tumor Cell Transmigration In Vitro

A signaling deficient CCL2 chemokine decoy with enhanced GAG-binding affinity was previously shown to inhibit recruitment of inflammatory leukocytes in vivo (Piccinini, A. M., Knebl, K., Rek, A., Wildner, G., Diedrichs-Mohring, M., and Kungl, A. J. (2010) *J Biol Chem* 285, 8782-8792). To further improve the therapeutic potential of CCL2-based decoys, the chemokine has been additionally engineered and fused to human serum albumin (HSA) in order to extend the serum half-life and to optimize the GAG-binding protein displacement profile with the aim to avoid off-target effects (manuscript in preparation). First, we tested the affinity of the unfused CCL2 mutant, designated as dnCCL2; and the HSA-coupled-dnCCL2, designated as GAGbody (FIGS. 7A and 7B) towards heparin using SPR measurement. We observed significantly enhanced affinity of both dnCCL2 and GAGbody compared to CCL2 (FIG. 6A). Next we tested dnCCL2 and GAGbody for their activity to block monocyte recruitment. Both compounds inhibited monocyte chemotaxis in the rage of 20-2000 nM when compared to CCL2 (FIG. 6B). Finally, dnCCL2 was verified for its biological activity in a murine system, which we selected for the analysis of CCL2-CCR2 axis in cancer progression. We tested the capacity of dnCCL2 to affect monocyte-facilitated tumor cell (MC-38GFP) transmigration through a monolayer of pulmonary microvascular endothelial cells using the Boyden chamber assay (FIG. 2C). While monocytes clearly potentiated endothelial transmigration of tumor cells (Qian, B. Z., Li, J., Zhang, H., Kitamura, T., Zhang, J., Campion, L. R., Kaiser, E. A., Snyder, L. A., and Pollard, J. W. (2011) *Nature* 475, 222-225), (Wolf, M. J., et al., (2012) *Cancer Cell* 22, 91-105) the presence of dnCCL2 at 10 or 100 µg/ml significantly attenuated this process. In contrast, there was no effect on tumor cell transmigration in the presence of a CCR5 inhibitor (Maraviroc) or low molecular weight heparin—Tinzaparin. These data indicate that the GAG-mediated CCL2-CCR2 chemokine axis is critical for an efficient tumor cell transendothelial migration and more importantly that dnCCL2 is biologically active also in a murine cell-based system.

Figure 8:
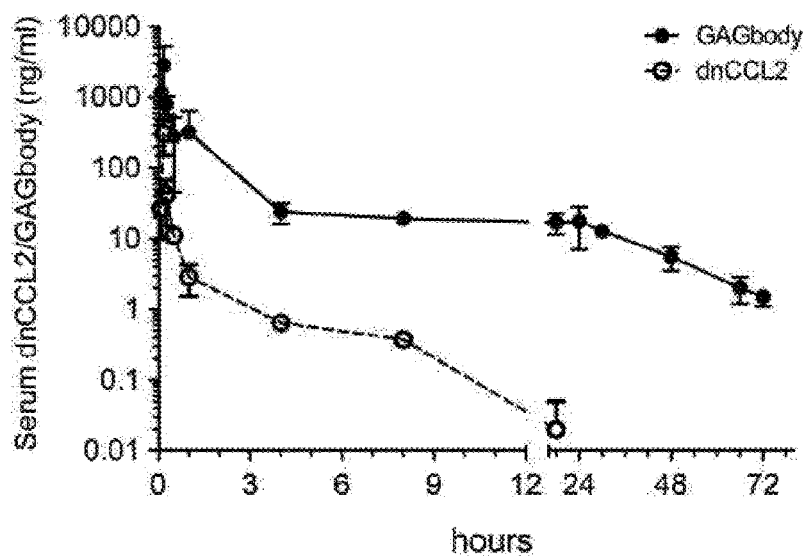

Biological Availability of GAGbody In Vivo was Enhanced Upon Conjugation to Human Serum Albumin To assess the biological potential of GAGbody in vivo, we first tested its pharmacokinetic profile compared to dnCCL2 in circulation upon intravenous injection (FIG. 8). As expected, dnCCL2 was almost completely cleared from the circulation within 24 h. The fusion construct HSA-linker-CCL2 mutant=GAGbody (ATG01, FIG. 7B) exhibited a significantly improved serum half-life and remained detectable even after 72 h (FIG. 8). The GAGbody™ was next used in a metastatic mouse model.

GAGbody Reduces Tumor Cell Induced Vascular Permeability and Formation of Metastatic Foci In Vivo Next, we tested whether GAGbody treatment affects lung vascular permeability, which is dependent on tumor-derived CCL2 and endothelial CCR2 expression (Wolf, M. J., et al., (2012) *Cancer Cell* 22, 91-105). Mice treated with GAGbody showed reduced vascular leakiness compared to untreated mice as determined by Evans blue assay 24 h post-tumor cell injection (FIG. 4G). To determine whether reduced vascular permeability in presence of GAGbody affects tumor cell seeding to the lungs and their extravasation, we analyzed lungs of mice intravenously injected with MC-38GFP cells after 6 h, 12 h, 24 h and 48 h. Indeed, GAGbody treatment significantly reduced the number of living tumor cells in the lungs at 24 h when compared to control (untreated) lungs and remained reduced also after two days (FIG. 4H). These findings indicate that temporal inhibition of the CCL2-CCR2 axis by GAGbody diminishes the ability of tumor cells to leave the vasculature.

GAGbody Treatment Reduces Pulmonary Metastasis

To test our hypothesis as to whether the CCL2 decoy protein inhibits metastatic formation in the lungs, we used experimental metastasis model using MC-38GFP cells. We treated mice intravenously with the dnCCL2 or GAGbody 10 min prior to tumor cell injection and 24 h post-tumor cell injection. Significant reduction of lung metastasis was observed in mice treated with GAGbody™ at two different concentrations, 17.5 µmol=200 µg and 70 µmol=800 µg resp., after 28 days (FIG. 9A-B). However, equimolar concentration of dnCCL2 (70 µmol=100 µg) did not have any effect on metastasis. Similarly, mice treatment with HSA alone had no effect on metastasis (FIG. 9A-B). Thus, we concluded that the prolonged serum half-life of the GAGbody is responsible for the antimetastatic activity when compared to dnCCL2. GAGbody treatment of mice prior to injection of using Lewis Lung carcinoma cells (3LL) also attenuated metastasis (FIG. 9C). This data confirmed that GAG-mediated CCL2-CCR2 axis promotes metastatic initiation, and a specific inhibition of CCL2 accumulation can inhibit this process.

Using the inventive mutant proteins, the inventors have not detected a reduced infiltration of inflammatory monocytes ($Ly6C^{hi}$) to the lungs 12 hours after intravenous tumor cell injection in GAGbody-treated compared to control mice. Despite, the inventors showed evidence for reduced vascular permeability upon GAGbody treatment and reduced metastasis. Finally, CCL2-decoy inhibitor diminished tumor cell transmigration through endothelium in the presence of monocytes in vitro, which is in agreement with previous data. These findings strongly indicate that targeting of vascular activation through CCL2 is the major mechanism how GAGbody lead to reduced metastasis.

The mechanism of GAGbody action appears to be different when compared to CCL2-neutralizing antibody. The inventors show that GAGbody efficiently binds to vascular GAGs in the lungs, thereby altering the intravascular activity of chemokines. The inventors also did not observe altered leukocytes numbers in the peripheral blood. On contrary, systemic use of CCR2 inhibitor affected also the levels of circulating inflammatory monocytes that can be explained by efficient targeting of the highly vascular bone marrow, thereby directly affecting the egress of monocytes from the bone marrow (28). Hence, GAGbody treatment is likely affecting the local metastatic microenvironment in the target tissue (lungs), and interferes with endothelial activation.

Example 3

Materials

GAG binding plates, LMW heparin, HMW heparin, heparan sulfate and dermatan sulfate were purchased from Iduron (Manchester, UK), all chemicals, unless stated otherwise, from Sigma-Aldrich (St. Louis, Mo., USA). CCL2, dnCCL2 and HSA(C34A)-(Gly)$_4$Ser-dnCCL2 were generated in house (see below). Phosphate-buffered saline (PBS) pH 7.2 contains 10 mM phosphate buffer and 137 mM NaCl.

Expression and Purification

Expression and Purification of dnCCL2

Mutant genes were synthesized from DNA2.0 and were obtained in the pJExpress411 expression vector for further transformation into BL21 (DE3) Star *E. coli* cells (Invitrogen, Carlsbad, Calif., USA).

Starting cultures were prepared and used for protein expression. Cultures were grown in 3-liter Erlenmeyer flasks under 200 rpm shaking at 37° C. in LB broth containing 30 µg/mL Kanamycin to an A600 of 0.8. Protein production was induced by the addition of 0.5 mM isopropyl β-D-thiogalactopyranoside. Cells were incubated with shaking for additional 3 hours and harvested by centrifugation for 15 minutes at 6000 g. Further expression and purification was performed as described earlier (Piccinini, et al., 2010, *Journal of biological chemistry*, 285, 8782-8792).

Protein Expression and Purification of the HSA(C34A)-(Gly)$_4$Ser-dnCCL2 Mutant

Expression of HSA(C34A)-(Gly)$_4$Ser-dnCCL2 was carried out using *Pichia pastoris* as expression host in a 1 L Multifors bioreactor (Infors AG, Bottmingen, Switzerland). The two-step fermentation process comprised a growth phase on glycerol followed by a production phase on methanol as sole carbon source. *P. pastoris* CBS7435 mut$^s$-PDI strain was inoculated in a starting volume of 0.4 L of fermentation medium (½ BSM containing 40 g/L glycerol) at a temperature of 28° C. and pH 5.0. The temperature was phased-down from 28 to 24° C. and pH was increased to 6.0 during the last 2 h of glycerol fed-batch and maintained at that level throughout the production time. The cultivation resulted in 6.5 g/L of the target protein with 62% purity.

To further purify the full length HSA(C34A)-(Gly)$_4$Ser-dnCCL2 a two-step purification was performed. In the first step a strong cation exchange resin—Fractogel EMD SO3—(Merck, Darmstadt Germany)—which was specifically interacting with the chemokine part of the construct, was used. The second step was an affinity chromatography resin, Blue Sepharose 6 Fast Flow (GE Healthcare, Chalfont St Giles, UK), which is Cibacron™ Blue 3G covalently attached to the Sepharose 6 Fast Flow matrix by the triazine coupling method. The blue dye binds many proteins, such as albumin, interferon, lipoproteins and blood coagulation factors. Furthermore it binds several enzymes including kinases, dehydrogenases, and most enzymes requiring adenyl-containing cofactors e.g., NAD+ (from GE Instruction manual for Bluespharose 6 Fast Flow).

For the initial purification step the supernatant obtained from *Pichia pastoris* fermentation was diluted 1:2 using a 50 mM Tris pH 8 buffer (low salt buffer) and subsequently loaded on Fractogel EMD SO3—pre-equilibrated in low salt buffer. The elution was performed by applying a linear gradient from 0 to 2 M NaCl in 50 mM Tris pH 8 over 10 CV. The protein containing fractions were pooled and diluted 1:12 in low salt buffer for the second purification step. The diluted protein solution was loaded on Bluesepharose 6 Fast Flow pre-equilibrated in 50 mM Tris pH 8. The elution was carried out as described for the first step. Concentrating of the protein was performed by ultrafiltration using Amicon Ultra-15 (Ultracef-3k, Millipore, Billerica, Mass., USA). Buffer exchange was performed by dialysis against PBS. To enhance the binding affinity of the HSA (C34A)-(Gly)$_4$Ser-dnCCL2 a third purification step was added. For this step the cation exchange resin SP Sepharose Fast Flow (GE Healthcare, Chalfont St Giles, UK) was used with the same buffers as mentioned before. Elution, Buffer exchange to PBS and concentrating were carried out as described above. The protein concentration was determined by UV280 measurement.

SDS-PAGE and Western Blotting

The purity of the protein was analysed by SDS/PAGE using 4-12% XT Criterion Precast gels (Biorad, Hemel Hempstead, UK) followed by Silver-staining, according to EMBL. For Western blot analysis, proteins were transferred via semi-dry blot (Biorad) onto PVDF membranes, blocked with 5% (w/v) non-fat dried skimmed milk powder in PBS for 1 h at room temperature (20° C.). Incubation with primary and secondary antibodies was carried out at room temperature for 1 h. All proteins were detected using α-MCP1 antibody sc-1304 (SantaCruz Biotechnology; Dallas, Tex., USA) diluted 1:200 and 1:10000 anti-goat IgG/HRP antibody (Sigma Aldrich, St. Louis, Mo., US) both diluted in dry milk. All proteins were visualized with the Immun star WesternC Kit (Biorad) and documented using the molecular imager Chemidoc XRS+ (Biorad) (Goger et al., 2002, *Biochemistry*, 41, 1640-1646).

Size-Exclusion Chromatography (SEC)

The SEC experiments were carried out on a Hitachi HPLC L-2100 system (Tokyo, Japan) equipped with an autosampler. A GE Superdex 75 PC 3.2/30 column (GE Healthcare, Chalfont St Giles, UK) was used for separation. The flow rate of the separation buffer was 0.05 ml/min and it was composed of 136 mM sodium chloride, 8 mM sodium phosphate dibasic and 1.9 mM sodium phosphate monobasic in $dH_2O$. The temperature of the column oven was set to 25° C. and the detection was conducted at 214 nm. Prior to the measurement each sample was diluted with separation buffer to a concentration of 1 mg/ml and equilibrated for at least 30 min at 4° C.

Guanidine Hydrochloride (Gua.HCl) Induced Protein Unfolding

The unfolding experiments were performed on a Jasco FP-Fluorometer FP6500 (Easton, Md., USA) coupled to an external water bath to ensure constant temperature during the measurements. 700 nM protein solutions in PBS containing different concentrations of guanidine hydrochloride ultra pure (MP Biomedicals, Solon, Ohio, USA) in the range of 0-6 M were prepared and equilibrated for 5 min at 20° C. Protein fluorescence emission spectra were recorded over the range of 300-400 nm upon excitation at 280 nm. The slit widths were set at 5 nm for excitation and emission, scan speed at 500 nm/min and the temperature was set to 20° C. After background subtraction, the wavelength of the peak maxima were plotted against guanidine concentration and the sigmoid transition curves were fitted using the Boltzmann equation with Origin 8.0 (OriginLab Corporation, Microcal Inc., Northampton, Mass., U.S.A.).

Isothermal Fluorescence Titration (IFT)

IFT measurements were carried out as described earlier (Gerlza et al., 2014) with the exception that GAGbody measurements were recorded with slit widths set at 3 nm for excitation and emission and sensitivity was manually adjusted to 550 V. Titrations were performed with Heparin and Heparan Sulfate from Iduron, with additions between 50 nM to 1000 nM of ligand.

ELISA-Like Competition (ELICO)

Biotinylation of chemokines was performed as described recently (Gerlza, et al., 2014, *Molecules*, 19, 10618-10634).

ELICO Protocol 2.5 µg GAG/250 nM biotinylated chemokine were diluted in PBS and coated on specially prepared Iduron plates over night at RT. A washing step was performed to remove unbound biotinylated chemokine and GAG, followed by a 2 h incubation with different competitor concentrations diluted in PBS starting from 100 µM to 6 nM for decoy chemokines and 200 µM to 12 nM for wt chemokines, measuring each concentration thrice. To detect the remaining biotinylated chemokine we used an ELISA-like setup, therefore after another washing step we incubated the plates with high sensitivity Streptavidin HRP (Thermo Scientific, Waltham, Mass., USA) diluted in 0.2% dry milk that binds to the non-displaced biotinylated chemokine on the plate. After another hour incubation at RT and removal of unbound Streptavidin by a washing step, we analysed the plate by adding the substrate Tetramethylbenzidine (TMB), resulting in a blue colour change. After stopping the reaction with sulphuric acid the absorbance at 450 nm was read in a Beckman Coulter DTX 800 Multimode Detector (Beckman Coulter, Austria). The reference ($OD_{620}$) values were subtracted from the sample values ($OD_{450}$) and the Mean and Standard Deviation was calculated. Data analysis was performed using specialized statistical software Origin® (GE Healthcare, Chalfont St Giles, UK).

GAG Binding Affinity

In order to assess whether the fusion to HSA has changed the GAG-binding affinity of the dnCCL2 mutant, various GAG-binding affinity experiments were performed. Kd values of CCL2, dnCCL2 and HSA(C34A)-(Gly)$_4$Ser-dnCCL2 to heparin and to heparan sulfate were determined using isothermal fluorescence titration (IFT). By this method, similar Kd values in the range of 200 nM were detected for dnCCL2 and HSA(C34A)-(Gly)$_4$Ser-dnCCL2, whereas wild type CCL2 exhibited the expected significantly lower affinity for both heparan sulfate (Kd=1138 nM) and heparin (Kd=2232 nM).

The bimolecular affinity between dnCCL2 and GAGs is apparently not significantly influenced by the HSA fusion. This is in accordance with the structural prediction of our molecular model (data not shown). However, it seems that although dnCCL2 is able to discriminate between heparin and heparan sulfate, the fusion mutant is not able to differentiate between these two GAG ligands. This loss of differentiation capability may be due to protection of amino acids in the fusion construct which are responsible for specific hydrogen bonding and/or hydrophobic interactions with the glycan in the unfused protein.

Selective Chemokine Displacement: ELISA-Like Competition (ELICO)

So far we have considered direct, i.e. bimolecular binding of GAGs to chemokine and chemokine mutants. We have recently established a method which allows quick and reliable determination of IC50 values for a given GAG-binding protein in relation to other pre-bound proteins from surface-immobilized GAGs (Gerlza, et al., 2014). We have called this method ELICO since the remaining protein in the reaction wells is quantified in an ELISA-like set-up. For this purpose, the pre-bound protein needs to be biotinylated for which we have developed efficient and reproducible methods which guarantee that the biotinylated protein is still able to bind to GAGs with the same (or very similar) affinity as the unlabeled protein (Gerlza, et al., 2014). In the current experiments we have evaluated how efficiently our chemokine (fusion) mutants not only displace their corresponding wild type protein but also other chemokines from heparan sulfate. The rationale behind these experiments is that displacement of too many unrelated chemokines from the same GAG ligand refers to a rather unspecific interaction of the chemokine mutant under investigation with GAGs. As a potential drug, this could cause unwanted off-target effects. To evaluate the displacement pattern of our mutants we have biotinylated several chemokines. From these, CCL2, CCL3, CCL5, CCL11, CXCL8, CXCL11, and CXCL12 were selected based mainly on bio-equivalence considerations (i.e. GAG binding and chemotaxis) after biotinylation compared to the unlabeled chemokines. Since many chemokines changed their bioactivity significantly after biotinylation, the assessment of a larger chemokine panel was not possible.

Regarding the displacement of wild type CCL2 (4), the HSA(C34A)-(Gly)$_4$Ser-dnCCL2 fusion construct gave an IC50 value of 2.3 µM. This is significantly better (2-fold) compared to CCL2 competing against CCL2, but not as good as the displacement capacity of dnCCL2 which gave an IC50 value of 82 nM. When specificity in the displacement pattern was considered by monitoring the displacement of chemokines other than CCL2, we observed that dnCCL2 displaced five more chemokines from HS (in addition to CCL2), whereas HSA(C34A)-(Gly)$_4$Ser-dnCCL2 displaced only two more (namely CCL5 and CXCL8, see FIG. 13).

This means that the HSA fusion mutant is a much more selective competitor than the dnCCL2 mutant, and resembles more closely the displacement profile of CCL2. An explanation as to why dnCCL2 is a less selective competitor can be most probably be attributed to its larger accessible surface area since this mutant exhibits a significantly lower oligomerisation state even compared to wtCCL2 (see FIG. 15). Consequently, dnCCL2 is able to either directly compete with other chemokines for their cognate GAG binding motif or to interact with the pre-bound chemokine to for hetero-oligomers (Jansma et al., 2009, *Methods in Enzymology*. Academic Press, pp. 31-50) which leads indirectly to dissociation from the GAG ligand.

Interestingly, both dnCCL2 and the HSA(C34A)-(Gly)$_4$Ser-dnCCL2 mutant displaced CCL5 and CXCL8 better (i.e. with lower IC50 values) than they displaced the CCL2 wild type. It can be assumed that the heparin and HS preparation we have used for identifying the CCL2 mutant with highest affinity did not represent (exclusively) the CCL2-specific GAG. Consequently, dependent upon the occurrence of a certain chemokine-specific GAG sequence in the GAG preparation under investigation, entirely unexpected and unspecific displacement profiles can be obtained. What we therefore need to consider in the future is the use of the chemokine mutant a chemokine-specific GAG preparations for the mutant affinity maturation.

Size-Exclusion Chromatography (SEC)

The quaternary structure of chemokines and chemokine mutants plays an important role in chemokine function (Fernandez and Lolis, 2002, *Annual review of pharmacology and toxicology*, 42, 469-499). Many chemokines were found to exist in solution as dimers or in larger oligomeric structures. CCL2 for example was found mainly as a tetramer in solution (Lau, et al., 2004, *Journal of biological chemistry*, 279, 22294-22305). GAG binding induces further aggregation of chemokines which efficiently increases the local concentration of chemokines at the site of their secretion thereby marking the hot spot of the chemotactic gradient (i.e. the site of highest concentration). On the contrary, as a way to induce the attenuation of the gradient, we have earlier proposed a negative impact of chemokine oligomerisation on GAG binding affinity. Since we have observed that oligomeric chemokines have significantly lower affinities towards GAGs than the monomeric or dimeric forms, we put forward a negative feedback model in which chemokines detach from GAG chains once they have oligomerised beyond a certain grade which correlates with high chemokine concentrations.

It was therefore important to see, whether the introduced modifications had an impact on quaternary structure formation. As can be seen in FIG. 15, wild type CCL2 displayed a dominant peak which corresponds to the CCL2 tetramer (apparent molecular weight: 21.2 kDa) and a shoulder at longer retention times representing the dimeric form of the chemokine (apparent molecular weight: 15.1 kDa). In contrast to this, the unfused chemokine mutant dnCCL2 eluted from the size exclusion column mainly as a dimer, no larger aggregates were observed. Finally, the HSA(C34A)-(Gly)$_4$Ser-dnCCL2 fusion mutant migrated on the SEC as monomer (apparent molecular weight: 75.6 kDa). This means that scaffolding the CCL2 mutant onto HSA led to an obligate monomer of the target chemokine.

Example 4

Isothermal Fluorescence Titration (IFT)

IFT measurements were carried out as described earlier (Gerlza et al., 2014) with the exception that the measurements were recorded with slit widths set at 3 nm for excitation and emission and sensitivity was manually adjusted to 550 V. Titrations were performed with Heparan Sulfate from Iduron, with additions between 50 nM to 1000 nM of ligand (see FIG. 16).

Binding of an HSA/IL-8 Fusion Mutant ATG03 to Heparan Sulfate (HS)

In FIG. 16 we show the binding isotherms derived by IFT for wild type IL-8, the unfused IL-8 mutant PA309 and the fusion protein ATG03. It can be clearly seen that both mutants bind to HS with significantly higher affinity than the wild type chemokine. Therefore it can be concluded that fusion of IL-8 mutants to HSA does not interfere with the engineered higher GAG binding affinity.

The invention claimed is:

1. A glycosaminoglycan (GAG) binding monomeric fusion protein comprising:
   a. a GAG binding protein moiety having the sequence of SEQ ID NO:9;
   b. a human serum albumin (HSA) moiety comprising an HSA sequence; and
   c. a linker between the HSA moiety and the GAG binding protein moiety, wherein the linker has the sequence of SEQ ID NO: 5.

2. The fusion protein of claim 1, wherein the HSA moiety is linked to the C-terminus of the GAG binding protein moiety.

3. The fusion protein of claim 1, wherein the fusion protein comprises an N-terminal methionine.

4. The fusion protein of claim 1, wherein the HSA moiety comprises the sequence of SEQ ID NO:4.

5. A method for treating metastasis in lung tissue of a subject, comprising administering an effective amount of a composition comprising the fusion protein of claim 1 to the subject.

6. The method of claim 5, wherein the composition comprises a pharmaceutically acceptable carrier.

7. A glycosaminoglycan (GAG) binding monomeric fusion protein comprising:
   a. a GAG binding protein moiety having the sequence of SEQ ID NO:10;
   b. a human serum albumin (HSA) moiety comprising an HSA sequence; and
   c. a linker between the HSA moiety and the GAG binding protein moiety, wherein the linker has the sequence of SEQ ID NO: 5.

8. The fusion protein of claim 7, wherein the HSA moiety is linked to the C-terminus of the GAG binding protein moiety.

9. The fusion protein of claim 7, wherein the fusion protein comprises an N-terminal methionine.

10. The fusion protein of claim 7, wherein the HSA moiety comprises the sequence of SEQ ID NO:4.

* * * * *

SEQUENCE LISTING

<160> NUMBER OF SEQ ID NOS: 10

<210> SEQ ID NO 1
<211> LENGTH: 76
<212> TYPE: PRT
<213> ORGANISM: Homo sapiens

<400> SEQUENCE: 1

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 2

```
<211> LENGTH: 667
<212> TYPE: PRT
<213> ORGANISM: Artificial Sequence
<220> FEATURE:
<223> OTHER INFORMATION: HSA-fused MCP-1 protein

<400> SEQUENCE: 2
```

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Met Gln
            580                 585                 590

Pro Asp Ala Ile Asn Ala Pro Val Thr Cys Cys Ala Gln Phe Thr Lys
            595                 600                 605

Arg Lys Ile Lys Val Lys Arg Leu Ala Ser Tyr Arg Arg Ile Thr Ser
    610                 615                 620

Lys Lys Cys Pro Lys Glu Ala Val Ile Phe Lys Thr Ile Val Ala Lys
625                 630                 635                 640

Glu Ile Cys Ala Asp Pro Lys Gln Lys Trp Val Gln Asp Ser Met Asp
                645                 650                 655

His Leu Asp Lys Gln Thr Gln Thr Pro Lys Thr
            660                 665

<210> SEQ ID NO 3
<211> LENGTH: 667
<212> TYPE: PRT
<213> ORGANISM: Artificial Sequence
<220> FEATURE:
<223> OTHER INFORMATION: HSA-fused MCP-1 protein

<400> SEQUENCE: 3

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu Gly Gly Gly Ser Met Gln
            580                 585                 590

Pro Asp Ala Ile Asn Ala Pro Val Thr Cys Cys Ala Gln Phe Thr Asn
            595                 600                 605

Arg Lys Ile Lys Val Lys Arg Leu Ala Ser Tyr Arg Arg Ile Thr Ser
        610                 615                 620

Ser Lys Cys Pro Lys Glu Ala Val Ile Phe Lys Thr Ile Val Ala Lys
625                 630                 635                 640

Glu Ile Cys Ala Asp Pro Lys Gln Lys Trp Val Gln Asp Ser Met Asp
                645                 650                 655

His Leu Asp Lys Gln Thr Gln Thr Pro Lys Thr
                660                 665

<210> SEQ ID NO 4
<211> LENGTH: 585
<212> TYPE: PRT
<213> ORGANISM: Artificial Sequence
<220> FEATURE:
<223> OTHER INFORMATION: modified Human Serum Albumin

<400> SEQUENCE: 4

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ala Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 5
<211> LENGTH: 5
<212> TYPE: PRT

```
<213> ORGANISM: Artificial Sequence
<220> FEATURE:
<223> OTHER INFORMATION: Linker

<400> SEQUENCE: 5

Gly Gly Gly Gly Ser
1               5

<210> SEQ ID NO 6
<211> LENGTH: 585
<212> TYPE: PRT
<213> ORGANISM: Homo sapiens
<220> FEATURE:
<223> OTHER INFORMATION: wild type Human Serum Albumin

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320
```

```
Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 7
<211> LENGTH: 72
<212> TYPE: PRT
<213> ORGANISM: Homo sapiens
<220> FEATURE:
<223> OTHER INFORMATION: wild type Interleukin-8

<400> SEQUENCE: 7

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 8
<211> LENGTH: 656
```

```
<212> TYPE: PRT
<213> ORGANISM: Artificial Sequence
<220> FEATURE:
<223> OTHER INFORMATION: HSA-fused modified Interleukin-8

<400> SEQUENCE: 8
```

| | | | | | | | | | | | | | | |
|---|---|---|---|---|---|---|---|---|---|---|---|---|---|---|
| Asp | Ala | His | Lys | Ser | Glu | Val | Ala | His | Arg | Phe | Lys | Asp | Leu | Gly | Glu |
| 1 | | | | 5 | | | | | 10 | | | | | 15 |
| Glu | Asn | Phe | Lys | Ala | Leu | Val | Leu | Ile | Ala | Phe | Ala | Gln | Tyr | Leu | Gln |
| | | | 20 | | | | | 25 | | | | | 30 | | |
| Gln | Ala | Pro | Phe | Glu | Asp | His | Val | Lys | Leu | Val | Asn | Glu | Val | Thr | Glu |
| | | 35 | | | | | 40 | | | | | 45 | | | |
| Phe | Ala | Lys | Thr | Cys | Val | Ala | Asp | Glu | Ser | Ala | Glu | Asn | Cys | Asp | Lys |
| | 50 | | | | | 55 | | | | | 60 | | | | |
| Ser | Leu | His | Thr | Leu | Phe | Gly | Asp | Lys | Leu | Cys | Thr | Val | Ala | Thr | Leu |
| 65 | | | | | 70 | | | | | 75 | | | | | 80 |
| Arg | Glu | Thr | Tyr | Gly | Glu | Met | Ala | Asp | Cys | Cys | Ala | Lys | Gln | Glu | Pro |
| | | | | 85 | | | | | 90 | | | | | 95 | |
| Glu | Arg | Asn | Glu | Cys | Phe | Leu | Gln | His | Lys | Asp | Asp | Asn | Pro | Asn | Leu |
| | | | 100 | | | | | 105 | | | | | 110 | | |
| Pro | Arg | Leu | Val | Arg | Pro | Glu | Val | Asp | Val | Met | Cys | Thr | Ala | Phe | His |
| | | | 115 | | | | | 120 | | | | | 125 | | |
| Asp | Asn | Glu | Glu | Thr | Phe | Leu | Lys | Lys | Tyr | Leu | Tyr | Glu | Ile | Ala | Arg |
| | 130 | | | | | 135 | | | | | 140 | | | | |
| Arg | His | Pro | Tyr | Phe | Tyr | Ala | Pro | Glu | Leu | Leu | Phe | Phe | Ala | Lys | Arg |
| 145 | | | | | 150 | | | | | 155 | | | | | 160 |
| Tyr | Lys | Ala | Ala | Phe | Thr | Glu | Cys | Cys | Gln | Ala | Ala | Asp | Lys | Ala | Ala |
| | | | | 165 | | | | | 170 | | | | | 175 | |
| Cys | Leu | Leu | Pro | Lys | Leu | Asp | Glu | Leu | Arg | Asp | Glu | Gly | Lys | Ala | Ser |
| | | | 180 | | | | | 185 | | | | | 190 | | |
| Ser | Ala | Lys | Gln | Arg | Leu | Lys | Cys | Ala | Ser | Leu | Gln | Lys | Phe | Gly | Glu |
| | | | 195 | | | | | 200 | | | | | 205 | | |
| Arg | Ala | Phe | Lys | Ala | Trp | Ala | Val | Ala | Arg | Leu | Ser | Gln | Arg | Phe | Pro |
| | 210 | | | | | 215 | | | | | 220 | | | | |
| Lys | Ala | Glu | Phe | Ala | Glu | Val | Ser | Lys | Leu | Val | Thr | Asp | Leu | Thr | Lys |
| 225 | | | | | 230 | | | | | 235 | | | | | 240 |
| Val | His | Thr | Glu | Cys | Cys | His | Gly | Asp | Leu | Leu | Glu | Cys | Ala | Asp | Asp |
| | | | | 245 | | | | | 250 | | | | | 255 | |
| Arg | Ala | Asp | Leu | Ala | Lys | Tyr | Ile | Cys | Glu | Asn | Gln | Asp | Ser | Ile | Ser |
| | | | 260 | | | | | 265 | | | | | 270 | | |
| Ser | Lys | Leu | Lys | Glu | Cys | Cys | Glu | Lys | Pro | Leu | Leu | Glu | Lys | Ser | His |
| | | | 275 | | | | | 280 | | | | | 285 | | |
| Cys | Ile | Ala | Glu | Val | Glu | Asn | Asp | Glu | Met | Pro | Ala | Asp | Leu | Pro | Ser |
| | 290 | | | | | 295 | | | | | 300 | | | | |
| Leu | Ala | Ala | Asp | Phe | Val | Glu | Ser | Lys | Asp | Val | Cys | Lys | Asn | Tyr | Ala |
| 305 | | | | | 310 | | | | | 315 | | | | | 320 |
| Glu | Ala | Lys | Asp | Val | Phe | Leu | Gly | Met | Phe | Leu | Tyr | Glu | Tyr | Ala | Arg |
| | | | | 325 | | | | | 330 | | | | | 335 | |
| Arg | His | Pro | Asp | Tyr | Ser | Val | Val | Leu | Leu | Leu | Arg | Leu | Ala | Lys | Thr |
| | | | 340 | | | | | 345 | | | | | 350 | | |
| Tyr | Glu | Thr | Thr | Leu | Glu | Lys | Cys | Cys | Ala | Ala | Ala | Asp | Pro | His | Glu |
| | | | 355 | | | | | 360 | | | | | 365 | | |
| Cys | Tyr | Ala | Lys | Val | Phe | Asp | Glu | Phe | Lys | Pro | Leu | Val | Glu | Glu | Pro |
| | 370 | | | | | 375 | | | | | 380 | | | | |

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Cys Gln
            580                 585                 590

Cys Ile Lys Thr Tyr Ser Lys Pro Phe His Pro Lys Phe Ile Lys Glu
        595                 600                 605

Leu Arg Val Ile Glu Ser Gly Pro His Cys Ala Asn Thr Glu Ile Ile
    610                 615                 620

Val Lys Leu Ser Asp Gly Arg Glu Leu Cys Leu Asp Pro Lys Glu Asn
625                 630                 635                 640

Trp Val Gln Arg Val Val Glu Lys Phe Leu Lys Arg Ala Lys Lys Ser
                645                 650                 655

```
<210> SEQ ID NO 9
<211> LENGTH: 666
<212> TYPE: PRT
<213> ORGANISM: Artificial Sequence
<220> FEATURE:
<223> OTHER INFORMATION: modified MCP-1
<220> FEATURE:
<221> NAME/KEY: UNSURE
<222> LOCATION: 586
<223> OTHER INFORMATION: Xaa is G, S or absent
<220> FEATURE:
<221> NAME/KEY: UNSURE
<222> LOCATION: 587
<223> OTHER INFORMATION: Xaa can be G, S or absent
<220> FEATURE:
<221> NAME/KEY: UNSURE
<222> LOCATION: 588
<223> OTHER INFORMATION: Xaa can be G, S or absent
<220> FEATURE:
<221> NAME/KEY: UNSURE
<222> LOCATION: 589
<223> OTHER INFORMATION: Xaa can be G, S or absent
<220> FEATURE:
<221> NAME/KEY: UNSURE
<222> LOCATION: 590
<223> OTHER INFORMATION: Xaa can be G, S or absent
<220> FEATURE:
```

<221> NAME/KEY: UNSURE
<222> LOCATION: 607
<223> OTHER INFORMATION: Xaa is N, R, K, H or Q
<220> FEATURE:
<221> NAME/KEY: UNSURE
<222> LOCATION: 611
<223> OTHER INFORMATION: Xaa is S, K, H, N or Q
<220> FEATURE:
<221> NAME/KEY: UNSURE
<222> LOCATION: 613
<223> OTHER INFORMATION: Xaa is R, K, H, N or Q
<220> FEATURE:
<221> NAME/KEY: UNSURE
<222> LOCATION: 624
<223> OTHER INFORMATION: Xaa is S, K, H, N or Q

<400> SEQUENCE: 9

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
```

325                 330                 335
Arg His Pro Asp Tyr Ser Val Val Leu Leu Arg Leu Ala Lys Thr
            340                 345                 350

Tyr Glu Thr Thr Leu Glu Lys Cys Cys Ala Ala Asp Pro His Glu
        355                 360                 365

Cys Tyr Ala Lys Val Phe Asp Glu Phe Lys Pro Leu Val Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Xaa Xaa Xaa Xaa Gln Pro
        580                 585                 590

Asp Ala Ile Asn Ala Pro Val Thr Cys Cys Ala Gln Phe Thr Xaa Arg
    595                 600                 605

Lys Ile Xaa Val Xaa Arg Leu Ala Ser Tyr Arg Arg Ile Thr Ser Xaa
610                 615                 620

Lys Cys Pro Lys Glu Ala Val Ile Phe Lys Thr Ile Val Ala Lys Glu
625                 630                 635                 640

Ile Cys Ala Asp Pro Lys Gln Lys Trp Val Gln Asp Ser Met Asp His
            645                 650                 655

Leu Asp Lys Gln Thr Gln Thr Pro Lys Thr
        660                 665

<210> SEQ ID NO 10
<211> LENGTH: 656
<212> TYPE: PRT
<213> ORGANISM: Artificial Sequence
<220> FEATURE:
<223> OTHER INFORMATION: modified Interleukin-8
<220> FEATURE:
<221> NAME/KEY: UNSURE
<222> LOCATION: 586
<223> OTHER INFORMATION: Xaa is G, S or absent
<220> FEATURE:
<221> NAME/KEY: UNSURE
<222> LOCATION: 587

```
<223> OTHER INFORMATION: Xaa is G, S or absent
<220> FEATURE:
<221> NAME/KEY: UNSURE
<222> LOCATION: 588
<223> OTHER INFORMATION: Xaa is G, S or absent
<220> FEATURE:
<221> NAME/KEY: UNSURE
<222> LOCATION: 589
<223> OTHER INFORMATION: Xaa is G, S or absent
<220> FEATURE:
<221> NAME/KEY: UNSURE
<222> LOCATION: 590
<223> OTHER INFORMATION: Xaa is G, S or absent
<220> FEATURE:
<221> NAME/KEY: UNSURE
<222> LOCATION: 601
<223> OTHER INFORMATION: Xaa is R, K, H, N or Q
<220> FEATURE:
<221> NAME/KEY: UNSURE
<222> LOCATION: 605
<223> OTHER INFORMATION: Xaa is R, K, H, N or Q
<220> FEATURE:
<221> NAME/KEY: UNSURE
<222> LOCATION: 654
<223> OTHER INFORMATION: Xaa is R, K, H, N or Q
<220> FEATURE:
<221> NAME/KEY: UNSURE
<222> LOCATION: 655
<223> OTHER INFORMATION: Xaa is R, K, H, N or Q

<400> SEQUENCE: 10

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Xaa Xaa Xaa Xaa Cys Gln
            580                 585                 590

Cys Ile Lys Thr Tyr Ser Lys Pro Xaa His Pro Lys Xaa Ile Lys Glu
        595                 600                 605

Leu Arg Val Ile Glu Ser Gly Pro His Cys Ala Asn Thr Glu Ile Ile
    610                 615                 620

Val Lys Leu Ser Asp Gly Arg Glu Leu Cys Leu Asp Pro Lys Glu Asn
625                 630                 635                 640

Trp Val Gln Arg Val Val Glu Lys Phe Leu Lys Arg Ala Xaa Xaa Ser
                645                 650                 655
```